(12) United States Patent
Reynolds, IV et al.

(10) Patent No.: US 9,984,322 B2
(45) Date of Patent: *May 29, 2018

(54) MEASUREMENT PROBE WITH HEAT CYCLE EVENT COUNTER

(71) Applicant: Broadley-James Corporation, Irvine, CA (US)

(72) Inventors: William E. Reynolds, IV, Irvine, CA (US); Robert J. Garrahy, Walnut, CA (US); Andrew W. Hayward, Flitwick (GB); Robert Fish, Rancho Cucamonga, CA (US); Jared H. Nathanson, Mission Viejo, CA (US); Bradley Joseph Sargent, Mission Viejo, CA (US); Scott T. Broadley, Laguna Beach, CA (US)

(73) Assignee: Broadley-James Corporation, Irvine, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/249,254

(22) Filed: Aug. 26, 2016

(65) Prior Publication Data

US 2017/0116510 A1 Apr. 27, 2017

Related U.S. Application Data

(63) Continuation of application No. 14/853,750, filed on Sep. 14, 2015, now Pat. No. 9,430,881, which is a (Continued)

(51) Int. Cl.
*G06M 1/10* (2006.01)
*G07C 3/00* (2006.01)
(Continued)

(52) U.S. Cl.
CPC ............... *G06M 1/10* (2013.01); *A61L 2/07* (2013.01); *G01K 13/02* (2013.01); *H02J 7/0054* (2013.01);
(Continued)

(58) Field of Classification Search
CPC ............. G06M 1/02; G06M 1/10; G07C 3/00
(Continued)

(56) References Cited

U.S. PATENT DOCUMENTS 4,235,842 A * 11/1980 Thomas ................. A61L 12/04
116/221
5,090,033 A * 2/1992 Murray-Shelley ... H03K 21/403
377/15

(Continued)

FOREIGN PATENT DOCUMENTS

DE 10 2007 039 088 A1 2/2009

OTHER PUBLICATIONS

International Search Report and Written Opinion of the International Searching Authority for International Application No. PCT/US2014/025025, dated Sep. 9, 2014.

*Primary Examiner* — William Hernandez
(74) *Attorney, Agent, or Firm* — Knobbe Martens Olson & Bear LLP

(57) ABSTRACT

A system comprising a measurement device and a handheld device is disclosed, the system adapted to withstand, detect, record, and display heat cycle event counts. The measurement device comprises a sensor for measuring and a heat cycle detection unit. The heat cycle detection unit comprises a temperature or pressure responsive element, a detection module, data interface, and data memory. The handheld device comprises a screen, a button, a communication circuit, and a processing system. The communication circuit is configured to communicate with the measurement device (Continued)

and a computing device and the processing system is configured to receive non-measurement information from the measurement device, display the received information on the screen, and cycle the received information displayed on the screen based on an actuation of the button, wherein the handheld device is used to display a heat sterilization cycle count of the measurement device.

22 Claims, 14 Drawing Sheets

Related U.S. Application Data continuation-in-part of application No. 14/801,625, filed on Jul. 16, 2015, now Pat. No. 9,430,880, which is a continuation of application No. 14/207,347, filed on Mar. 12, 2014, now Pat. No. 9,117,166, and a continuation-in-part of application No. PCT/US2014/025025, filed on Mar. 12, 2014.

(60) Provisional application No. 61/794,355, filed on Mar. 15, 2013.

(51) Int. Cl.
*H02J 50/10* (2016.01)
*H02J 7/00* (2006.01)
*G01K 13/02* (2006.01)
*A61L 2/07* (2006.01)
*H02J 7/34* (2006.01)

(52) U.S. Cl.
CPC ........... *H02J 50/10* (2016.02); *A61L 2202/14* (2013.01); *H02J 7/345* (2013.01)

(58) Field of Classification Search
USPC ........................................ 377/15, 19, 25, 26
See application file for complete search history.

(56) References Cited

U.S. PATENT DOCUMENTS

| | | | |
|---|---|---|---|
| 5,359,993 A * | 11/1994 | Slater | A61B 1/00062 |
| | | | 116/216 |
| 5,452,335 A * | 9/1995 | Slater | A61B 17/00234 |
| | | | 377/25 |
| 5,991,355 A * | 11/1999 | Dahlke | A61B 18/14 |
| | | | 377/15 |
| 6,166,538 A | 12/2000 | D'Alfonso | |
| 6,295,330 B1 | 9/2001 | Skog | |
| 2005/0183656 A1* | 8/2005 | Isaacson | A61B 18/12 |
| | | | 116/216 |
| 2011/0034910 A1 | 2/2011 | Ross | |

* cited by examiner

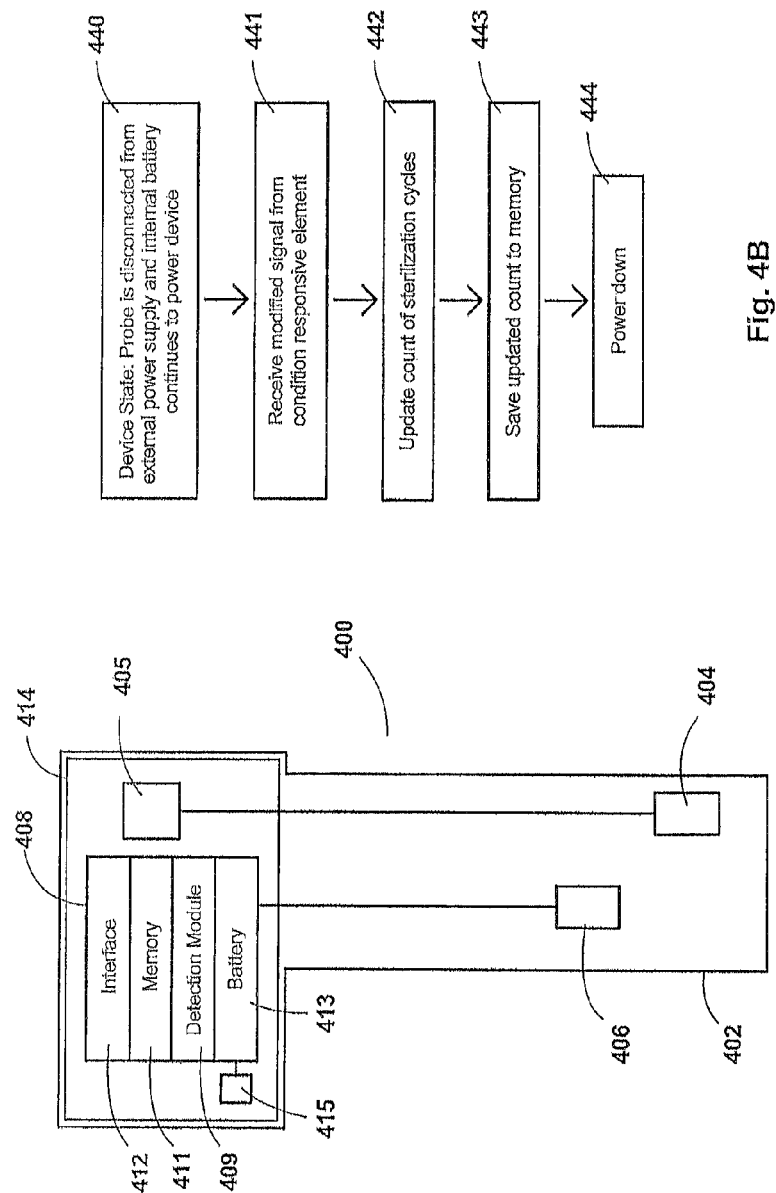

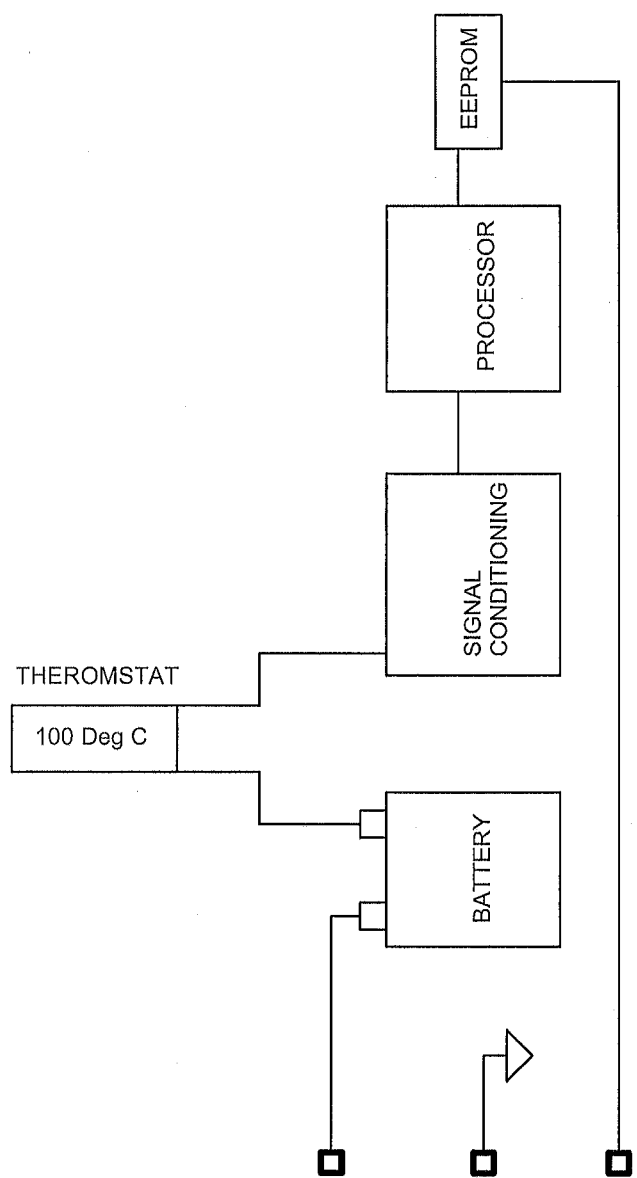

MEASUREMENT PROBE WITH HEAT CYCLE EVENT COUNTER

CROSS-REFERENCES TO RELATED APPLICATIONS

This application is a continuation of U.S. patent application Ser. No. 14/853,750, filed Sep. 14, 2015, which is a continuation-in-part of U.S. patent application Ser. No. 14/801,625, filed Jul. 16, 2015, which is a continuation of U.S. patent application Ser. No. 14/207,347, filed Mar. 12, 2014, granted as U.S. Pat. No. 9,117,166, on Aug. 25, 2015, which claims priority benefit of U.S. Provisional Patent Application No. 61/794,355, filed Mar. 15, 2013; U.S. patent application Ser. No. 14/853,750, filed on Sep. 14, 2015, is a continuation-in-part of Patent Cooperation Treaty Application No. PCT/US2014/025025, filed Mar. 12, 2014, which claims priority benefit of U.S. Provisional Application No. 61/794,355, filed Mar. 15, 2013; each of the aforementioned applications are incorporated by reference in its entirety herein.

BACKGROUND

Field of the Invention

The present invention relates to measurement probes. More particularly, the invention relates to devices and methods used to detect and count heat cycles experienced by measurement probes.

Description of the Related Art

Control of industrial processes is largely dependent on measurement signals received from measurement devices within process mediums. Measurement probes, which are equipped with sensors such as pH sensors, temperature sensors, redox sensors, carbon dioxide sensors, and dissolved oxygen sensors, are frequently used to monitor biological and chemical processes in the fields of biotechnology, pharmaceuticals, and food/beverage processing. In such industries, accuracy of measurements is critical.

In such industries, sterilization or cleaning is also critical. Frequent sterilization or cleaning is often required in these industries. This may be because bacteria and other microorganisms may proliferate on unsterilized surfaces and create health risks. Alternatively, sterilization may help avoid introducing contaminants of competing microorganisms into a cell culture. Additionally, sterilization or cleaning of bioprocess vessels or pipes in which sensors are installed can expose the sensors to high temperatures and/or harsh chemicals that can introduce errors in the sensor's measurement signal or even lead to sensor failure.

Three sterilization or cleaning methods are frequently employed to sterilize equipment used in biological or chemical processes: steam-in-place sterilization, clean-in-place, and autoclaving. Steam-in-place sterilization procedures allow for in-line pressurized steam sterilization of all surfaces located within the interior of a reaction vessel or other processing container (herein referred to as a processing vessel), thus providing for sterilization without disassembly. Clean-in-place procedures allow for in-line cleaning by flushing the process vessel and associated piping with sanitizing chemical solutions at elevated temperatures. Autoclaving involves subjecting the processing vessel and the entire probe, to pressurized steam heat within a separate autoclave chamber. Autoclaving is often a preferred method of sterilization at least in part when the processing vessel is relatively small and transportable to the autoclave chamber. The major drawback to autoclaving is that the entire probe body is subjected to the high sterilization temperature and this can have a detrimental effect on any internal circuitry that is powered up at the time. If the probe is externally powered then it must be disconnected from its signal and/or power cable before it is placed in the autoclave. In many industries, subjecting the process vessel, probes, and associated equipment to high pressure steam at 121° C. in an autoclave for 20-30 minutes is sufficient to achieve sterilization. However, it is not uncommon to find that the vessel, probes, and associated equipment are exposed to pressurized steam at temperatures in excess of 130° C. and for periods of 60 minutes or longer to ensure complete sterilization.

Measurement probes can experience structural changes, aging, and decreased functionality and accuracy through exposure to extreme conditions. Particularly, the rapid increase and decrease of temperature associated with common steam heat sterilization or hot chemical solution cleaning methods may lead to probe degradation; thus, measurement probes are consumable products which must be replaced regularly. In industry, a balance is required when determining how frequently to replace measurement probes. Premature exchange of probes unnecessarily increases costs, whereas a probe that has reached the end of its life may fail during use. Loss of the probe measurement in mid-process often results in loss of process control and the subsequent ruin of an entire biological or chemical batch, leading to costly waste and delays. Accordingly, it is important for the probe operator to monitor the condition and evaluate the fitness for service of industrial measurement probes by tracking the number of heat cycles that it has experienced.

Additionally, the high temperatures a measurement probe may endure during a clean-in-place, steam-in-place, or autoclave operation may cause damage to the measurement probe or to its operation. While the high heat of the sanitizing operation may not physically affect the probe, operation at high heat may result in unexpected outcomes. Thus, in an embodiment, the measurement probe and the associated circuitry itself may be protected from high temperatures so as to protect the circuitry and the physical structure of the device. In another embodiment, the measurement probe and the associated circuitry may be protected from operating in high temperatures so as to avoid unexpected operations and outcomes and to avoid the possibility of errors in functionality and operation that may result from operating the measurement probe and associated circuitry at high temperatures.

SUMMARY

The present disclosure describes devices and methods used to detect and count heat cycles experienced by measurement probes, particularly heat cycles associated with steam heat sterilization and hot chemical solution cleaning procedures. These procedures are among the greatest contributors to probe degradation and failure. Accordingly, by providing means for detecting and maintaining a count of the heat cycles associated with these procedures, the devices and methods described herein will help probe operators determine the risk associated with continued use of the probe and determine when it is time to replace the measurement probes.

The embodiments disclosed herein each have several innovative aspects, no single one of which is solely responsible for the desirable attributes of the invention. Without limiting the scope, as expressed by the claims that follow, the more prominent features will be briefly disclosed here. After considering this discussion, one will understand how the features of the various embodiments provide several advantages over current measurement probes.

One aspect of the disclosure is an apparatus adapted to couple to a measurement device and display information acquired from the measurement device. The apparatus comprises a screen, a button, a connector configured to connect to the measurement device, a power source connector, a processing system, and a computing device connector. The processing system is configured to receive information from the measurement device, display the received information on the screen, and cycle the received information displayed on the screen based on an actuation of the button. The computing device connector is configured to electrically and physically couple the apparatus to a computing device.

In some embodiments, the power source comprises a battery configured to provide electrical power to the screen, the processing system, and the measurement device to allow the processing system to receive information from the measurement devices and display the received information on the screen. In some embodiments, the apparatus further comprises a memory configured to store the information received from the measurement device and information entered by a user via the button or the computing device coupled via the connector. In some embodiments, the information received from the measurement device comprises one or more of an identification information of the measurement device, a sterilization cycle count of the measurement device, a location of installation of the measurement device, one or more calibration parameters of the measurement device, one or more manufacturing data of the measurement device, and customer specific information of the measurement device.

In some embodiments, the one or more manufacturing data comprises a serial number, a manufacturer part number, performance data, and a date of calibration and performance tests, and the customer specific information comprises an experiment name with which the measurement device is associated, an operator's name with which the measurement device is associated, a lot number with which the measurement device is associated, and one or more customer defined fields. In some embodiments, the information received from the measurement device further comprises data measured by the measurement device.

Another aspect of the disclosure is a system. The system comprises a measurement device adapted to withstand and automatically count a heat sterilization or cleaning cycle and a handheld device. The handheld device comprises a screen, a button, a connector configured to couple the handheld device to a computing device, and a processing system. The processing system is configured to receive information from the measurement device, display the received information on the screen, and cycle the received information displayed on the screen based on an actuation of the button. The handheld device is used to display a heat sterilization cycle count of the measurement device connected to the handheld device.

In some embodiments, the computing device may be coupled to the handheld device and configured to perform at least one of calibrating the measurement device via the handheld device, viewing information stored in the measurement device via the handheld device, editing information stored in the measurement device via the handheld device, viewing information stored in the handheld device, and editing information stored in the handheld device. In some embodiments, the handheld device is further used to display one or more of calibration parameters of the measurement device, manufacturing data of the measurement device, and customer custom fields of the measurement device.

One aspect of the disclosure is a system comprising a measurement device and a handheld device or an apparatus comprising the measurement device. The handheld device comprises a screen, a button, a connector configured to couple with the measurement device, a connector configured to electrically and physically couple the handheld device to a computing device, and a processing system. The processing system is configured to receive information from the measurement device, display the received information on the screen, and cycle the received information displayed on the screen based on an actuation of the button. The handheld device is used to display a heat sterilization cycle count of the measurement device connected to the handheld device. The measurement device is adapted to withstand and automatically detect a heat sterilization or cleaning cycle and increment and maintain a counter of the total number of cycles for later review by the operator, particularly when the measurement device is disconnected from all external power sources. The measurement device includes a measurement probe including a sensor configured to detect a characteristic of a medium and generate a measurement signal; a condition responsive element including either a temperature responsive element or a pressure responsive element; and a heat cycle detection unit including a detection module, a data interface, and a data memory. The detection module is configured to detect a heat cycle event using the condition responsive element, and record detection of the heat cycle event in the data memory. In some embodiments the heat cycle event is part of an autoclave procedure, a steam-in-place sterilization procedure, or a clean-in-place procedure. In some embodiments the measurement device is configured to automatically power up the heat cycle detection unit as soon as the heat cycle is detected, the heat cycle detection unit then increments a counter, and then the measurement device powers itself off to protect the circuit from prolonged and excessive heat exposure as in the case of an autoclave procedure where the entire probe is autoclaved. In some other embodiments the measurement device will automatically turn itself back on when the heat cycle is complete and the measurement device has cooled off to a safe operating temperature. In some embodiments, the measurement device will automatically turn itself back on when the heat cycle is complete and the device has cooled off to a safe operating temperature, at which point the measurement device records the occurrence of the heat cycle, and then the measurement device automatically powers off until the next heat cycle is detected. In other embodiments the measurement device will remain off to conserve battery power and only turn itself back on briefly when another heat cycle is detected and the cycle needs to be counted by the heat cycle detection unit. In some embodiments, the measurement probe and the heat cycle detection unit are separably connected. In other embodiments, the measurement probe and the heat cycle detection unit are fixedly integrated.

In some embodiments, the condition responsive element is a first switch configured to transition from a first state to a second state when the first switch exceeds a first temperature or a first pressure. In such embodiments, the detection module is configured to record detection of a heat cycle event in the data memory in response to the first switch transitioning from the first state to the second state. The measurement device may further include a capacitor coupled to the first switch, which is configured to discharge in response to the first switch transitioning from the first state to the second state. In such embodiments, the detection module need not be powered up during an autoclave cycle but is configured to detect the discharged capacitor and record detection of a heat cycle event in the data memory after the autoclave detection unit is powered back on following an autoclave cycle. The first switch changes to its second state at some pre-defined temperature that marks the beginning of the heat cycle. This second state discharges a capacitor. When the detection module powers back up it detects the discharged capacitor and increments the event counter.

In some embodiments, the measurement device also includes a portable power source in addition to, or instead of, a capacitor. In such embodiments, the detection module is configured to record detection of a heat cycle event in the data memory in response to a temperature responsive element exceeding a first temperature or a pressure responsive element exceeding a first pressure. After the counter is incremented the autoclave detection unit is configured to power off in response to the temperature responsive element exceeding the first temperature or in response to the pressure responsive element exceeding the first pressure. In some such embodiments, the measurement device includes a second switch configured to transition from a power-off state to a power-on state when the second switch falls below a power-on temperature or a power-on pressure. In such embodiments, the autoclave detection unit is configured to automatically power on when the second switch transitions from the power-off state to the power-on state. In some embodiments, the second switch and the condition responsive element are one and the same; a universal switch can acts as both the second switch and the condition responsive element.

The first switch and/or the second switch in various embodiments may be selected from the group consisting of: a bimetallic strip, an integrated thermal switch, and a pressure switch. The condition responsive element of other embodiments may be selected from the group consisting of: a resistance temperature detector, a bimetallic strip, an integrated thermal switch, a positive temperature coefficient thermistor, switching PCT thermistor, or other thermistor, a pressure switch, a reed switch, a piezoelectric pressure sensor, an electromagnetic pressure sensor, a capacitive pressure sensor, and a piezoresistive strain gauge. In various embodiments, the first temperature and/or power-on temperature are within a range of 50 to 120 degrees Celsius, and the first pressure and/or power-on pressure are within a range of 15 to 45 psi.

In some embodiments, the measurement device also includes a coupling element configured to engage with a vessel body such that, when the coupling element is engaged with the vessel body, the measurement device includes a distal portion that is positioned within a vessel cavity and a proximal portion that is positioned external to the vessel cavity. In some such embodiments, the condition responsive element is a distal condition responsive element, preferably positioned in or on the distal portion. In other embodiments, the condition responsive element is a proximal condition responsive element, preferably positioned in or on the proximal portion. When the measurement device comprises a proximal condition responsive element, the measurement device may additionally include a distal condition responsive element, preferably positioned in or on the distal portion. In such embodiments, the detection module is configured to detect a heat cycle event and record detection of the heat cycle event in the data memory in response to either the proximal condition responsive element exceeding a first temperature or pressure or the distal condition responsive element exceeding a vessel sterilization temperature or pressure. Additionally, in such embodiments, the detection module may be configured to detect an autoclave cycle and record detection of the autoclave cycle in the data memory in response to the proximal condition responsive element exceeding a first temperature or pressure, and the module may be further configured to detect a steam-in-place cycle and record detection of the steam-in-place cycle in the data memory in response to only the distal condition responsive element exceeding the vessel sterilization temperature or pressure. The autoclave detection unit can be configured to power off when an autoclave cycle is detected and optionally power off when a steam-in-place cycle is detected.

In some embodiments both a distal condition responsive element and a temperature responsive element located in the distal portion of the measurement device and another proximal condition responsive element. When a preset temperature limit is exceeded in the sterilization or cleaning procedure in the distal portion of the measurement device, the distal condition responsive element changes state and powers on the circuit in the detector module. The module then increments the heat cycle counter and additionally uses the temperature responsive element in the distal portion to measure additional information such as maximum heat exposure and length of exposure time in the case of steam-in-place or clean-in-place procedures. The proximal temperature responsive element is also powered on and it monitors the measurement device temperature at the proximal portion. If the proximal temperature exceeds a preset limit then the measurement device logic determines that the measurement device is being autoclaved and the circuit completely shuts down after incrementing the heat cycle counter.

In some embodiments, the measurement device also includes a pH sensor positioned in the distal portion. In one such embodiment, a distal condition responsive element, preferably, but not necessarily, located in the distal portion, can change state due to a process heat cycle and switch on the measurement device's power and the detection module can be configured to differentiate and detect a clean-in-place cycle and record detection of the clean-in-place cycle when a distal condition responsive element exceeds a clean-in-place temperature or pressure and a measurement from the pH sensor exceeds a clean-in-place pH level, both within a defined period of time. The distal condition responsive element of some embodiments is a temperature responsive element. In at least some embodiments, the clean-in-place temperature is within a range of 65 to 95 degrees Celsius, and the clean-in-place pH is within the extreme ranges of either 9 to 14 pH or 1 to 4 pH.

In various embodiments, the first temperature and/or the vessel temperature are within a range of 50 to 120 degrees Celsius, and the first pressure is within a range of 15 to 45 psi. The measurement probe is selected from the group consisting of an amperometric, a potentiometric, an optical, a capacitive, and a conductive probe. Additionally, in some embodiments, the sensor is selected from the group consisting of a pH sensor, a temperature sensor, a dissolved oxygen sensor, and a combination thereof. The detection module of some embodiments is selected from the group consisting of a circuit, a microprocessor, a Digital Signal Processor, an Application Specific Integrated Circuit, and a Field Programmable Gate Array. The data interface of some embodiments is selected from the group consisting of a wireless transmitter, an input/output terminal, a data bus, galvanic metal connector contacts, a contactless inductive coupling interface (see e.g. DE 19540854A1, DE 4344071A1, and U.S. Pat. Nos. 8,639,467, 7,785,151, 6,705,898, 6,476,520, 5,325,046, and 5,293,400; each of which is incorporated herein by reference in its entirety and for disclosure thereof), and an industry standard 8 pin connector. In some embodiments, the measurement device also includes a power-gathering system, such as, for example, a photodiode or a photovoltaic cell. In some embodiments, the data interface and/or the data output may allow for communication of signals and data via a secondary (or relay) device, as will be discussed in further detail below.

An additional aspect of the disclosure is a method of automatically counting autoclave and other heat sterilization cycles and/or cleaning cycles experienced by any embodiment of the measurement device described above, while protecting the circuitry contained within the measurement device and managing the measurement device's power supply. The method includes detecting a heat sterilization cycle using a first temperature responsive element that is configured to respond when the temperature exceeds a first temperature, automatically powering up the detection unit circuitry if off, recording detection of the heat sterilization cycle in a data memory and incrementing a counter, and automatically powering off the detection unit circuitry after detection of the heat sterilization cycle, if it is desired in a particular process procedure to protect the measurement device's circuit from malfunctioning due to excessive heat during the heat cycle and to conserve the measurement device's power.

Another aspect of the disclosure is a method of automatically counting a heat cycle experienced by a measurement device. The method includes providing a measurement device, the measurement device including a measurement probe having a sensor configured to detect a characteristic of a medium and generate a measurement signal, a condition responsive element, and a heat cycle detection unit having a detection module, a data interface, and a data memory. The method further includes detecting a heat cycle event, using the condition responsive element and recording detection of the heat cycle event in the data memory. In some embodiments, the heat cycle event is an autoclave cycle, a steam-in-place sterilization event, or a clean-in-place event. In some embodiments, the measurement device is configured to automatically power up the heat cycle detection unit after detection of the heat cycle event and then, after incrementing the counter, power it down if the heat cycle event comprises an autoclave cycle.

In some embodiments of the method, the condition responsive element is a first switch that transitions from a first state to a second state when the first switch exceeds a first temperature or a first pressure, and the detection module records detection of a heat cycle event in the data memory in response to the first switch transitioning from the first state to the second state. In some such embodiments, the method also includes discharging a capacitor coupled to the first switch in response to the first switch transitioning from the first state to the second state. In such embodiments, detecting a heat cycle event using the condition responsive element involves detecting a discharged capacitor. In some such embodiments, detecting a discharged capacitor and recording detection of a heat cycle event in the data memory occur after the autoclave detection unit is powered on following an autoclave cycle.

In some embodiments of the method, the autoclave detection unit receives power from a portable power source electrically coupled to the measurement device. The detection module of some such embodiments records detection of a heat cycle event in the data memory in response to the condition responsive element exceeding a first temperature or a first pressure. The autoclave detection unit of some such embodiments powers off in response to the condition responsive element exceeding the first temperature or the first pressure. In some embodiments, the method additionally includes automatically powering on the autoclave detection unit when a second switch in the measurement device transitions from a power-off state to a power-on state. In such embodiments, the second switch transitions from the power-off state to the power-on state when the second switch falls below a power-on temperature or pressure. In some embodiments, a universal switch within the measurement device includes both the second switch and the condition responsive element.

In various embodiments of the method, the first temperature and/or the power-on temperature are within a range of 50 to 120 degrees Celsius, and the first pressure and/or the power-on pressure are within a range of 15 to 45 psi.

The method of some embodiments also includes engaging with a vessel body such that a distal portion of the measurement device is positioned within a vessel cavity and a proximal portion of the measurement device is positioned external to the vessel cavity. In some embodiments, the condition responsive element is positioned in or on the distal portion. In other embodiments, the condition responsive element is positioned in or on the proximal portion.

In some embodiments having a proximal condition responsive element, preferably positioned in or on the proximal portion, the detection module detects a heat cycle event and records detection of the heat cycle event in the data memory in response to either the proximal condition responsive element exceeding a first temperature or first pressure or a distal condition responsive element, preferably positioned in or on the distal portion, exceeding a vessel sterilization temperature or pressure. In some such embodiments, the step of detecting a heat cycle event and recording detection of the heat cycle event in the data memory includes one of: detecting an autoclave cycle and recording detection of the autoclave cycle in the data memory in response to the proximal condition responsive element exceeding a first temperature or a first pressure, or detecting a steam-in-place cycle and recording detection of the steam-in-place cycle in the data memory in response to the distal condition responsive element exceeding the vessel sterilization temperature or pressure and the proximal condition responsive element not exceeding a first temperature or a first pressure. In some such embodiments, the autoclave detection unit powers off when an autoclave cycle is detected and optionally powers off when a steam-in-place cycle is detected.

In the method of some embodiments, the detection module detects a clean-in-place cycle and records detection of the clean-in-place cycle when: (1) a distal condition responsive element, preferably located in or on the distal portion exceeds a clean-in-place temperature or pressure, and (2) a measurement from a pH sensor positioned in the distal portion exceeds a clean-in-place pH level, both within a defined period of time. In some such embodiments, the distal condition responsive element, preferably located in or on the distal portion, is a temperature responsive element.

In some embodiments of the method, the clean-in-place temperature is within a range of 65 to 90 degrees Celsius and/or the clean-in-place pH is within a range of either 9 to 14 pH or 1 to 4 pH. Additionally or alternatively, in some embodiments, the first temperature and the vessel temperature are within a range of 50 to 120 degrees Celsius and the first pressure is within a range of 15 to 45 psi. In any of the embodiments disclosed herein, the data interface may be selected from the group consisting of a wireless transmitter, an input/output terminal, a data bus, and an industry standard 8 pin connector. In any of the embodiments disclosed herein, the measurement device may further comprise an inductive or wireless coupling connector, wherein the inductive or wireless coupling connector is configured to permit transfer of wherein at least one of energy, power, and data are transferred via optical, inductive or wireless coupling between the measurement device and at least one of an external power supply or transmitter, optionally via a relay device. In any of the embodiments disclosed herein, at least one of an energy, a power, and a data may be transferred via optical, inductive or wireless coupling between the measurement device and at least one of an external power supply or transmitter, optionally via a relay device.

Another aspect provides a system comprising a measurement device and a handheld device. The measurement device is adapted to withstand and automatically count a heat sterilization or cleaning cycle. The measurement device comprises a measurement probe, a condition responsive element, and a heat cycle detection unit. The measurement probe comprises a sensor configured to detect a characteristic of a medium and generate a measurement signal. The condition responsive element comprises either a temperature responsive element or a pressure responsive element. The heat cycle detection unit comprises a detection module, a data interface, and a data memory and is configured to detect a heat cycle event using the condition responsive element and record detection of the heat cycle event in the data memory. The measurement device is configured to automatically power off the heat cycle detection unit after detection of the heat cycle. The handheld device is connected to the measurement device and comprises a screen, a button, a communication circuit configured to communicate with the measurement device and a computing device, and a processing system. The processing system is configured to receive non-measurement information from the measurement device, display the received information on the screen, and cycle the received information displayed on the screen based on an actuation of the button. The handheld device is used to display a heat sterilization cycle count of the measurement device.

An additional aspect provides a method for automatically counting and displaying a heat cycle experienced by a measurement device. The method comprises providing a measurement device. The measurement device comprises a measurement probe having a sensor configured to detect a characteristic of a medium and generate a measurement signal, a condition responsive element, and a heat cycle detection unit having a detection module, a data interface, and a data memory. The method further comprises detecting a heat cycle event, using the condition responsive element, recording detection of the heat cycle event in the data memory, connecting to and communicating with a handheld device, and displaying information communicated from the measurement device to the handheld device on a screen of the handheld device. The information displayed on the handheld device comprises a heat sterilization cycle count of the measurement device.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

FIG. 4A depicts a block diagram of another embodiment of a measurement device.

FIG. 4B is a flowchart illustrating one method of operations performed by the measurement device of FIG. 4A.

FIG. 11 depicts a schematic circuit diagram for an embodiment of a heat cycle detection unit.

DETAILED DESCRIPTION OF VARIOUS EMBODIMENTS

Figure 1:
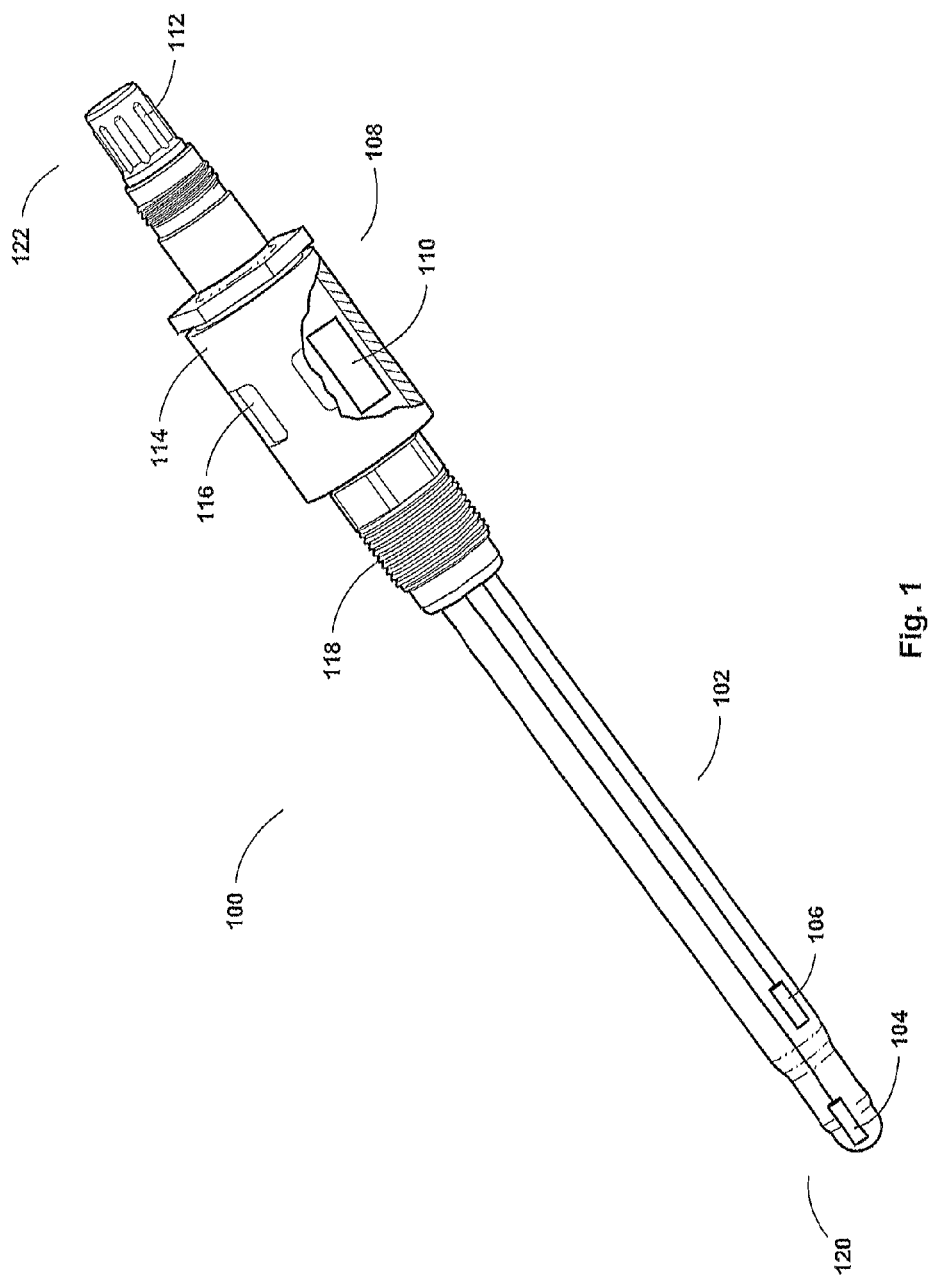
FIG. 1 depicts a perspective view of one embodiment of a measurement device.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. "Connected" and "coupled," and variations thereof, as used herein include direct connections, such as being contiguously formed with or attached directly to, on, within, etc. another element, as well as indirect connections where one or more elements are disposed between the connected elements. "Connected" and "coupled" may refer to a permanent or non-permanent (i.e., removable) connection. "Connected" and "coupled" may refer to both wired and wireless connections, for example, a wireless connection or coupling may include a connection or coupling allowing for wireless power transfer and/or wireless communication.

"Secured" and variations thereof as used herein include methods by which an element is directly fastened to another element, such as being glued, screwed or otherwise affixed directly to, on, within, etc. another element, as well as indirect means of attaching two elements together where one or more elements are disposed between the secured elements.

"Proximal" and "distal" are relational terms used herein to describe position. For clarity purposes only, in this disclosure, position is viewed from the perspective of an individual operating a measurement device positioned partially within a processing vessel. The portion of the measurement device located external to the vessel is viewed as being closest, and therefore, most proximal to the operator. The portion of the device positioned within the container is more distally located.

As used herein, "proximal condition responsive element," "distal condition responsive element," "proximal temperature responsive element," "distal temperature responsive element," "proximal pressure responsive element," and "distal pressure responsive element," and their equivalents are used to describe the locations to which the condition, temperature or pressure responsive element are responsive, and not necessarily where the element is located. For example, a distal condition responsive element is responsive to conditions occurring at/in the distal portion of a probe, and can be located in the distal portion of the probe, or can be located in the proximal portion of the probe but configured to be responsive to conditions at/in the distal portion of the probe. As a non-limiting example, a pressure sensing element located in the proximal portion of the probe could be in fluid communication with the interior of the distal portion of the probe, such that changes in pressure in the distal portion of the probe are sensed by the pressure sensor located in the proximal portion of the probe—such a pressure sensor is "distal condition responsive element" or "distal pressure responsive element" because it is responsive to conditions in/at the distal portion of the probe. In another example, a proximal condition responsive element is responsive to conditions occurring in the proximal portion of the measurement probe, but could be located in the proximal portion, the distal portion, or outside the measurement probe.

The terms "automatically" or "autonomously" as used herein are intended to identify devices capable of taking an action without external input from a user or other device. As a non-limiting example, such an action includes turning on and/or turning off a portion or all of the device. An energy or power autonomous device may be capable of managing its energy or power free from external connections. For example, an energy or power autonomous device may comprise a photovoltaic cell or a battery. In one example, a device may activate on demand by waking up or powering on based upon sensed conditions to perform a task and going to sleep or powering off after the task is complete without external commands.

Various sensors or switches may be utilized in the invention as described herein. These sensors and switches may detect various conditions that a measurement probe may face during operation and maintenance. In some embodiments, these sensors and switches may monitor temperature. In another embodiment, these sensors and switches may monitor pressures. In some other embodiments, these sensors and switches may monitor a combination of temperature and/or pressure. Sensors and switches that may monitor pressure may be configured so as to monitor atmospheric pressure or internal pressure of the measurement probe. A sensor or switch that monitors atmospheric pressure may be intended to measure the pressure of the environment outside the measurement probe. A sensor or switch that monitors internal pressure may be intended to measure the pressure internal to the measurement probe. A sensor or a switch that monitors internal pressure may be used to detect a temperature change where the measurement probe is sealed, such that a temperature change of the measurement probe creates a pressure change internal to the measurement probe that may be detected by the internal pressure sensor or switch.

In some embodiments, a pressure condition responsive element (pressure sensor or switch) may be configured to respond to pressure condition changes within the proximal portion of the measurement probe, wherein the pressure within the proximal portion is isolated from the pressure within the distal portion. In such an embodiment, the pressure condition responsive element may be configured to respond to either internal pressure changes or atmospheric pressure changes. Such a pressure change of the proximal portion may indicate the measurement probe is experiencing an autoclave cycle. In another embodiment, a pressure condition responsive element may be configured to respond to pressure changes within the distal portion of the measurement probe, wherein the pressure within the proximal portion is isolated from the pressure within distal portion. In such an embodiment, the pressure condition responsive element may be configured to respond to internal pressure changes. Such pressure changes of the distal portion may indicate the measurement probe is experiencing any heat cycle involving elevated temperatures or pressures but may not allow for the distinguishing between an autoclave cycle and a clean-in-place or steam-in-place cycle.

There is a need for a measurement probe that monitors and quantifies its own usage and operational fitness in the bioprocess industries. A leading cause of probe degradation in bioprocess applications is the thermo shock associated with the increase and decrease of temperature associated with some heat sterilization procedures that utilize pressurized steam and cleaning procedures that utilize hot sanitizing chemical solutions. A bioprocess industry standard for keeping track of wear on a measurement probe is the number of these heat cycles experienced by the probe. In some applications, probes are exposed to no more than two to ten heat cycles before being retired. In other applications, the count may be higher. The particular number of heat sterilization or cleaning cycles that a probe can withstand varies by probe manufacturer, sterilization or cleaning method, operator maintenance, and the environmental conditions within the processing medium; thus, probe operators familiar with their unique uses and processes are best equipped to predict the lifespans of their respective probes. Currently, however, in bioprocess laboratory and production settings, it is often easy to lose track of the number of heat sterilization or cleaning cycles experienced by each probe.

Accordingly, there is more than one probe design currently on the market that is configured to detect and record steam-in-place sterilization cycles. However, the design of such probes renders them inoperable during autoclave cycles. In the current models, the probes must be unplugged and fully powered down before being placed in an autoclave chamber; as a result, they can neither detect nor count autoclave cycles. Without being able to automatically detect and count this widely used sterilization method, in many bioprocess applications the current generation of sterilization-counting probes provides little benefit over conventional probe designs. In addition, probes are often disconnected from external power sources during steam-in-place cycles to avoid damaging cables which may come in contact with steam supply pipes or the hot vessel wall. Probes which require an external power source to detect and record steam-in-place cycles will not record the steam-in-place event if the operator disconnects the probe cables.

Another existing probe design uses recorded temperature and time-at-temperature data to self-calculate the length of its remaining lifespan. However, these calculations can provide probe lifespan estimates that are not particularly accurate for the application at hand. This can lead the process operator into a false sense of safety as he reuses a probe that self-predicts that it has ample lifespan remaining and then the probe fails. Lifespans vary across industries and companies and are dependent on nearly innumerable factors. Additionally, the cost of probe failure, and thus, the willingness to accept risk of probe failure, varies across companies.

Various embodiments disclosed herein may overcome some or all of the deficiencies mentioned above. The embodiments relate to devices and methods used to monitor and quantify the usage and operational fitness of measurement probes by automatically (without user input) counting heat cycle events experienced by said probes, even when disconnected from external power supplies. The measurement devices of various embodiments are each configured to detect exposure to heat sterilization or hot chemical cleaning cycles, including autoclave cycles, steam-in-place cycles and/or clean-in-place cycles, and subsequently maintain an accurate count of the sterilization or cleaning cycles experienced. With such an accurate count, laboratory technicians and other probe operators may be able to easily and efficiently determine when it is time to order new probes and/or throw away existing probes based on their own unique experience with that particular bioprocess application. There is currently no commercial probe in the bioprocess industries that can automatically count and record to memory the number of autoclave cycles that it has experienced. The preferred embodiments disclosed herein provide an accurate count of the heat cycles completely automatically and with no operator input or assistance. It is completely automated.

These preferred devices also improve the accuracy of the heat cycle count for probes undergoing steam-in-place and clean-in-place procedures. These devices enable accurate heat cycles counts for probes even when not connected to associated instrumentation for any heat cycle procedure.

A measurement device representative of the various embodiments discussed in more detail below includes at least a measurement probe, a condition responsive element, and a heat cycle detection unit. The measurement probe may include a sensor configured to detect a characteristic of a medium and generate an electrical signal or a measurement signal representing a measured value relating to the characteristic, typically an analog or digital signal. The sensor can be any electrochemical sensor known to those skilled in the art. For example, in some embodiments, the sensor may be a pH sensor, a temperature sensor, a dissolved oxygen sensor, or a combination thereof. The measurement probe may be amperometric, potentiometric, optical, capacitive, conductive, or any other suitable probe type known to those skilled in the art.

In various embodiments, the condition responsive element is in the form of a temperature responsive element or a pressure responsive element. In the simplest embodiments, the condition responsive element may be a mechanical switch or other element that undergoes a physical transformation in response to an environmental trigger. For example, in some embodiments, the condition responsive element may be a bimetallic strip (also referred to as a thermostat or thermal switch) or a shape memory alloy, such as, for example, nickel-titanium (Nitinol), which undergoes a physical change in shape when the temperature rises above a certain threshold. In some embodiments, the materials are selected and configured such that the physical change occurs within a temperature range of 50 to 120 degrees Celsius, and more preferably, within a range of 100 to 115 degrees Celsius or an additional range of 60 to 110 degrees Celsius and any sub-range or value therebetween. For example, the physical transformation may occur at 50° C., 55° C., 60° C., 65° C., 70° C., 75° C., 80° C., 85° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., or 120° C., or a range defined by any two of these values.

In other embodiments, the condition responsive element is an integrated thermal switch or pressure switch, which opens or closes an electrical contact when a threshold temperature or pressure, respectively, has been reached. The threshold temperature may be within the range disclosed above. The threshold pressure may be within a range of 10 to 60 psi, and preferably, within a range of 15 to 45 psi. The threshold pressure may include any sub-range or value therebetween, including, for example, 15 psi, 16 psi, 17 psi, 18 psi, 19 psi, 20 psi, 21 psi, 22 psi, 23 psi, 24 psi, 25 psi, 26 psi, 27 psi, 28 psi, 29 psi, 30 psi, 31 psi, 32 psi, 33 psi, 34 psi, 35 psi, 36 psi, 37 psi, 38 psi, 39 psi, 40 psi, 41 psi, 42 psi, 43 psi, 44 psi, or 45 psi, or a range defined by any two of these values.

In still other embodiments, the condition responsive element is an electrical element, such as a resistive element, which produces a change in the electrical signal at least when a threshold value is reached. In some such embodiments, the threshold value may be any of the threshold temperatures and pressures disclosed above. In some embodiments, the condition responsive element may be a pressure switch or sensor or a temperature switch or sensor. The condition responsive element of some embodiments is, for example, a positive temperature coefficient thermistor, switching PCT thermistor, or other thermistor, a resistance temperature detector (RTD), a reed switch, a piezoelectric pressure sensor, an electromagnetic pressure sensor, a capacitive pressure sensor, a piezoresistive strain gauge, or any other suitable electrical component known to those skilled in the art.

The heat cycle detection unit preferably includes at least a detection module, a data memory, and a data interface. The detection module and data memory may be printed on stacked circuit cards. The detection module of some embodiments is a general purpose processor. In other embodiments, it is a Digital Signal Processor (DSP), an Application Specific Integrated Circuit (ASIC), a Field Programmable Gate Array (FPGA) or other programmable logic device, discrete gate or transistor logic, discrete hardware components, MEMS piezoelectric pressure sensors, a micro-pressure switches, diaphragm pressure switches, or any combination thereof designed to perform the functions described herein. A general purpose processor may be a microprocessor, but in the alternative, the processor may be any processor, controller, microcontroller, or state machine. A detection module may also be implemented as a combination of computing devices. In some embodiments, the detection module, data memory, data interface, and any other associated processors and processing circuitry associated with the heat cycle detection unit may be shared between the heat cycle detection unit and the measurement device. For example, the heat cycle detection circuitry may be used by the measurement device or measurement probe to perform any calculations or conversions (for example, converting a signal from analog to digital, or vice versa). Thus, in addition to the heat cycle counting functionality, the processing chips or circuitry may be integrated with any other processing or computing functionality of the measurement device or probe, reducing the need for duplicate components. Similarly, the memory of the heat cycle detection unit may be shared with various other components or computing or processing systems integrated into the measurement probe or device.

The data memory may include Random Access Memory (RAM), flash memory, Read Only Memory (ROM), Electrically Programmable ROM (EPROM), Electrically Erasable Programmable ROM (EEPROM), registers, hard disk, a micro-secure digital (SD) card or other removable disk, or any other suitable form of storage medium known in the art. The data memory is coupled to the detection module such that the module can read information from, and write information to, the data memory. In some but not all embodiments, the data memory is integral to the detection module. The detection module and the data memory of some embodiments reside in an ASIC. In alternative embodiments, the detection module and the data memory reside as individual discrete components. As described above, in some embodiments, the data memory may be used to store measurement data (for example, information that the measurement device measures when in operation, such as pH measurements from a pH measurement device) and non-measurement data (for example, information not measured by the measurement device, such as calibration information, model number, etc.).

The data interface may allow for the communication of signals and information from the detection module to a data output. In some embodiments, the detection module conditions and/or transforms electrical signals before they reach the data interface. Consequently, the data interface of various embodiments transmits analog and/or digital signals.

The data interface of some embodiments includes one or more radio frequency transmitters, other wireless transmitters, couplers, universal serial buses (USB) and/or other data buses. The data interface may comprise an eight-pin connector configured to physically and electrically couple to an external transmitter and power supply (not shown). Accordingly, the data interface may be configured to transfer power to/from the measurement device as well as communicate data. In some embodiments, the data interface may be configured to provide for power transfer and data communication concurrently or non-concurrently. In some embodiments, the measurement device includes an output component, such as, for example, a display screen or signal lights, to display processed data to a user. In other embodiments, the measurement device transmits the data to an external display screen or other output device via near-field communications, radio frequency signals, Bluetooth signals, or other wireless signals, or through a physical electrical connection (e.g., electrical wires, cables, or connector pins) or a contactless inductive coupling interface (see e.g. DE 19540854A1, DE 4344071A1, and U.S. Pat. Nos. 8,639,467, 7,785,151, 6,705,898, 6,476,520, 5,325,046, and 5,293,400; each of which is incorporated herein by reference in its entirety and for disclosure thereof). The data output of various embodiments includes, preferably, a count of autoclave cycles and/or total sterilization or cleaning cycles experienced by the device as well as probe serial ID number, manufactured date, and other meta data useful to the operator.

In some embodiments, the data interface and/or the data output may allow for bi-directional communication of signals and data via at least one of a physical connection, a wireless connection, an optical connection, or an inductive connection between the data interface and/or data output and an external device (or transmitter or base unit). In another embodiment, a secondary (e.g., relay) device may be configured to physically couple with the measurement device and allow bi-directional communication of signals and data to an external device (e.g., power supply, transmitter, or base unit) via a wireless, optical, inductive, or physical connection between the secondary device and the external device. In an alternate embodiment, the secondary device may be configured to wirelessly couple with the measurement device and provide for bi-directional communication and/or power transmission between the measurement device and an external power supply or transmitter. In some embodiments, the relay device may include a circuit having at least one controller and at least one memory region. The relay device may be configured to receive data and/or power from the external power supply or transmitter and forward the data and/or the power to the measurement device. Alternatively, the relay device may be configured to receive data and/or power from the measurement device and transmit the data to the external transmitter.

In some embodiments, the detection unit may be connected fixedly with a first element of a pluggable connector coupling, to which the measurement device housing is accommodated. A connection element (e.g., relay unit, a transmitter, other element or circuitry capable of processing a measurement signal, or a cable, etc.) may comprise a second element of the pluggable connector coupling, in which the circuitry of the connection element is accommodated, wherein, between the circuit of the measurement device and the circuitry of the connection element, data and/or energy are exchangeable via the pluggable connector coupling, when the first and second elements of the pluggable coupling are connected with one another. The pluggable connector coupling can be implemented by usual connectors with plug and socket, via which a galvanic connection is produced. Alternatively the pluggable connector coupling can provide galvanic isolation between the measurement device and the connection element by transmitting data and/or energy via an inductive, wireless, or optical coupling between the circuit of the measurement device and the circuitry of the connection element. Accordingly, the detection unit may be connected fixedly with a first element of the pluggable connector coupling and said circuit of the measurement device may be also accommodated in this first element. The connection element may be included in a second element of the pluggable connector coupling, and the circuit of the connection element may be accommodated in the second element. Between the circuit of measurement device and the circuit of the connection element, data and/or energy may be exchangeable via a pluggable connector coupling, when the first and second elements of the pluggable connector coupling are connected with one another. The pluggable connector coupling may provide galvanic isolation between the measurement device and the connection element by transmitting data and/or energy via a wireless, an inductive or optical coupling between the circuit of the sensor unit and the circuit of the connection element.

In some embodiments, the heat cycle detection unit additionally includes a protective housing or other casing that wholly or partially surrounds at least some of the electronic components of the measurement device. The housing may be configured to withstand high temperatures, such as, for example, at least temperatures up to 140 degrees Celsius, and/or from pressurized steam and moisture. The housing may be further configured to protect the electronic components disposed within the housing from such temperatures and/or moisture. The housing may encase stacked circuit cards on which the detection module and the data memory are printed. Additionally, the housing may include a plurality of glass or plastic-covered windows. The windows may be designed to permit the entrance of light into the interior of the housing. In such embodiments, one or more photodiodes or photovoltaic cells are included in the heat cycle detection unit to convert light energy into current or voltage. As described in more detail below, the photodiodes and photovoltaic cells are coupled to batteries and/or capacitors within the system to help replace leaking current or charge. In some embodiments, the windows are covered by a clear plastic or other suitable transparent material. Other embodiments include no windows or only one transparent window.

In some embodiments, the measurement probe and the heat cycle detection unit may be fixedly connected. In other embodiments, the measurement probe and the heat cycle detection unit may be separably coupled. In some such embodiments, the heat cycle detection unit forms, or is positioned within, a removable cap. In other embodiments, the heat cycle detection unit is positioned within a separate transmitter or dongle.

The measurement device may further includes a vessel-coupling element. The vessel-coupling element may be configured to interact with, and securely connect to, a receiving port in a processing vessel. Such receiving ports may be positioned on the side or in the lid of a processing vessel or in a pipe or channel that is fluidly connected to the processing vessel. The measurement device may couple to processing vessels via complementary threading. In other embodiments, a tri-clamp or other suitable connection means is used. Once connected, a distal portion of the measurement device, comprising at least the sensor, is positioned within an interior of the processing vessel. A proximal portion of the measurement device, comprising at least the data interface, is positioned outside the processing vessel.

Many of the steps of a method or algorithm and functions described in connection with the embodiments disclosed herein may be embodied directly in hardware, in a software module executed by a processor, or in a combination of the two. All such embodiments are contemplated and incorporated into use of the term: detection module. If implemented in software, the functions may be stored on, or transmitted over as, one or more instructions or code on a tangible, non-transitory computer-readable medium.

The steps the detection module is configured and/or programmed to perform include: detecting a sterilization or cleaning event using the condition responsive element, recording detection of the sterilization or cleaning event in the data memory, and automatically powering off the heat cycle detection unit and resetting the detection module to respond again to the next heat cycle event. The logic and processes needed to perform these functions are described in more detail below.

FIG. 1 depicts a perspective view of an exemplary embodiment of a measurement device. FIG. 1 is a generic structure in which the previously described elements are located in an exemplary fashion. The measurement device depicted may be representative of any of the embodiments discussed herein. The location and connections of the respective elements are intended to be exemplary and not limiting. Additional embodiments may not include all of the elements depicted and discussed in relation to FIG. 1. Those of skill in the art will understand that any combination of any number of elements depicted and described in relation to FIG. 1 may be combined in an embodiment of a measurement device.

FIG. 1 shows the measurement device 100 that may include at least a measurement probe 102, a condition responsive element 106, and a heat cycle detection unit 108. The measurement probe 102 may include a sensor 104. In some embodiments, the sensor 104 is a pH sensor, a temperature sensor, a dissolved oxygen sensor, or a combination thereof, while the measurement probe 102 can be amperometric, potentiometric, optical, capacitive, conductive, or any other suitable probe type known to those skilled in the art. In various embodiment, the condition responsive element 106 may be a temperature responsive element or a pressure responsive element.

The heat cycle detection unit 108 preferably includes at least a detection module, a data memory, and a data interface 112. In FIG. 1, the detection module and the data memory are not individually visible; however, they may be printed on stacked circuit cards 110.

Continuing with FIG. 1, the data interface 112 may comprise an eight-pin connector configured to physically and electrically couple to an external transmitter and power supply (not shown). In some embodiments, the heat cycle detection unit 108 additionally includes a protective housing 114 or other casing that wholly or partially surrounds at least some of the electronic components of the measurement device 100. Additionally, the housing 114 in FIG. 1 may include a glass or plastic-covered window 116. FIG. 1 depicts an embodiment where measurement probe 102 and heat cycle detection unit 108 are fixedly connected. FIG. 1 further includes a vessel-coupling element 118, which, when used to couple the measurement device 100 to a vessel, results in a proximal portion 122 of the measurement device 100 positioned outside the processing vessel, and a distal portion 120 position within an interior of the processing vessel.

Figure 2:
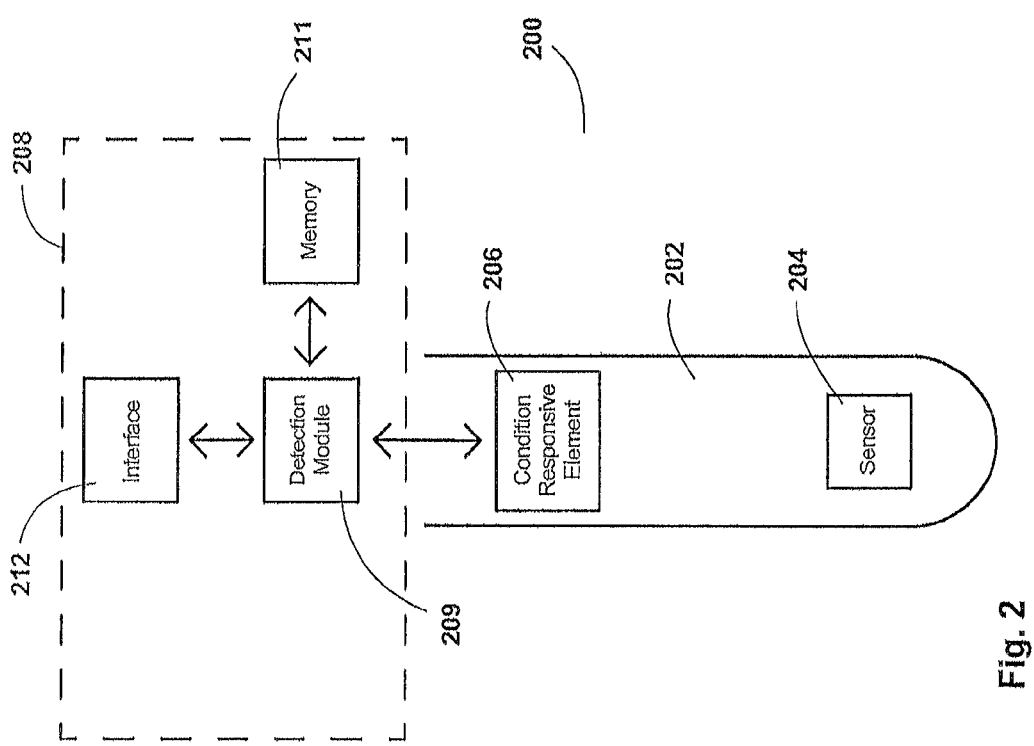
FIG. 2 depicts a block diagram of one embodiment of a measurement device.

In a basic embodiment, such as the embodiment depicted schematically in FIG. 2, the measurement device 200 includes a sensor 204 and a condition responsive element 206 positioned within, or coupled to, a measurement probe 202. The device also includes a heat cycle detection unit 208, which is preferably positioned within a transmitter, dongle, or removable cap. In some embodiments, the condition responsive element 206 is located in the heat cycle detection unit 208, rather than the measurement probe 202. In some embodiments, the heat cycle detection unit 208 is physically separable from the measurement probe 202. The heat cycle detection unit 208 includes a detection module 209, a data memory 211, and an interface 212. In one method of using the measurement device 200 of FIG. 2, the measurement probe 202 is disconnected from the heat cycle detection unit 208 and from any power source prior to being placed within an autoclave. Autoclaving is then initiated. The condition responsive element 206 deforms or otherwise changes shape in response to the temperature or pressure in the autoclave increasing to near or above a certain threshold. The set threshold for a given condition responsive element 206 is determined by the materials and configuration of the condition responsive element 206. The condition responsive element 206 may have a range of a few degrees within which it undergoes deformation. In some such embodiments, the condition responsive element 206 is a bimetallic strip or a shape memory alloy that deforms in response to an increase in temperature. In some embodiments, when the condition responsive element 206 deforms, it or another movable member in contact with the condition responsive element 206 mechanically locks into a second position, remaining in the second position even as the temperature drops. In one embodiment of the method, after the autoclaving is complete, the measurement probe 202 is removed from the autoclave and connected to the heat cycle detection unit 208. During or upon connection to the measurement probe 202, the heat cycle detection unit 208 detects the presence of an element locked in a second position. The heat cycle detection unit 208 resets the element, causing the element to move back to a first position, and the detection module 209 stores a sterilization or cleaning cycle (e.g. autoclave cycle) count in the data memory 211. Although in some embodiments the heat cycle detection unit comprises a pressure responsive element, and thus the heat cycle detection unit is responding to a pressure change or a pressure event rather than temperature events, those of skill in the art will understand that the change in pressure within the probe or atmospheric pressure outside the probe may be associated with an autoclave cycle and also signals that a heat cycle has occurred. As discussed above, the pressure event experienced and counted by the detection module 209 may depend upon the type of pressure event experienced. An atmospheric pressure event may indicate a pressure change in the atmospheric pressure (pressure outside the measurement device 200), which may result from an autoclave cycle. However, an internal pressure event may result from heating of the probe during either a sterilization or an autoclave cycle. Thus, an internal pressure event alone may be insufficient to distinguish a count by the detection module 209 between a clean-in-place/steam-in-place and an autoclave cycle, absent additional elements in the probe as described in other embodiments herein.

Figure 3B:
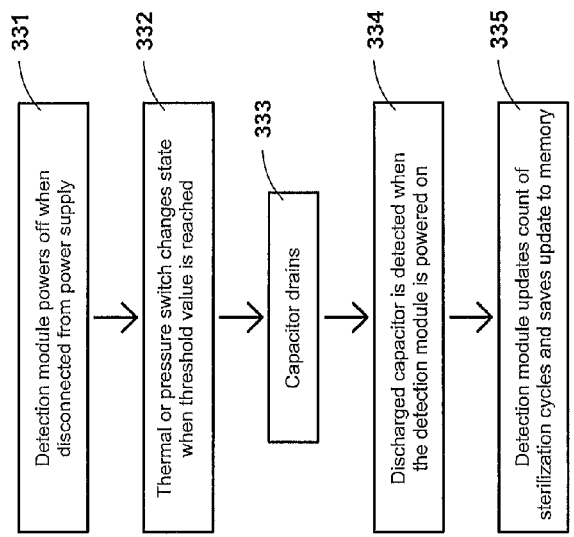
FIG. 3B is a flowchart illustrating one method of operations performed by the measurement device of FIG. 3A.
Figure 3A:
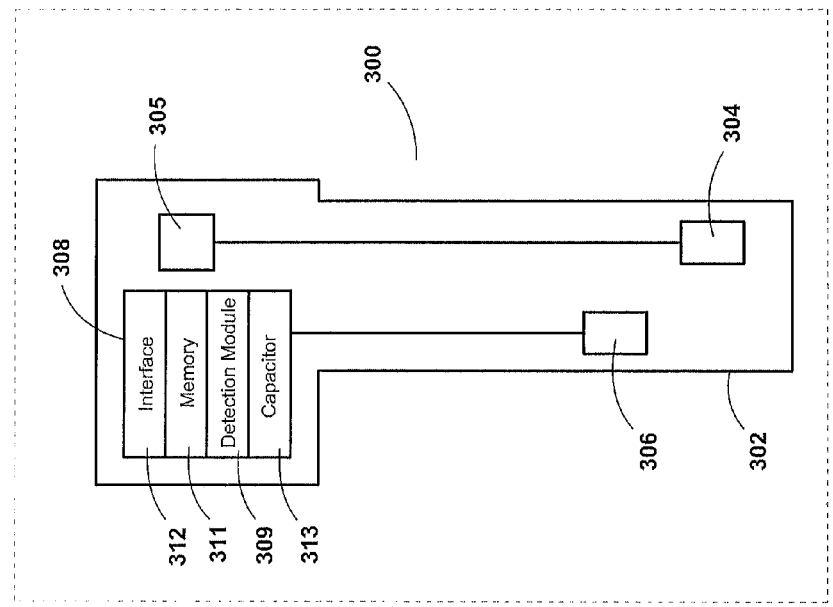
FIG. 3A depicts a block diagram of another embodiment of a measurement device.

FIG. 3A provides a schematic of another measurement device embodiment. In FIG. 3A, the measurement device 300 includes a measurement probe 302 having a sensor 304 electrically coupled to a measurement interface 305 and a condition responsive element 306 electrically coupled to a heat cycle detection unit 308. In some embodiments, the condition responsive element 306 is located in the heat cycle detection unit 308, rather than the measurement probe 302. The sensor 304 is electrically coupled to a measurement interface 305 configured to provide probe operators with information about the environmental condition being sensed by the measurement probe 302. The condition responsive element 306 is electrically connected to a heat cycle detection unit 308, which includes a detection module 309, a data memory 311, a capacitor 313, and an interface 312. In some embodiments, the interface 312 and interface 305 are the same interface.

A method of operations for the measurement device embodiment of FIG. 3A, is shown in the flowchart of FIG. 3B. When describing the functions of specific components, reference numbers from FIG. 3A will be used. At block 331, the measurement device 300 is disconnected from an external power supply, causing the detection module 309 to power down. The measurement device 300 can then be placed in an autoclave chamber and subjected to the high temperatures and pressures of an autoclave cycle. At block 332, the condition responsive element 306, which is in the form of a mechanical thermal switch or pressure switch, moves or deforms at a set threshold temperature or pressure value, respectively, with the set threshold value determined by the physical and chemical properties of the switch 306. The deformation/movement of the switch 306 closes an electrical contact within a circuit. As shown at block 333, the closing of the electrical contact within the circuit causes a capacitor or similar charge storage unit 313 to drain. In some embodiments, the switch 306 returns to a first, non-deformed position when the temperature or pressure falls below the threshold value, which returns the circuit to its first state. The capacitor remains drained until the measurement device 300 is reconnected to a power supply and additional current flows to the capacitor 313. As shown in block 334, after the measurement device 300 is reconnected to a power supply, the detection module 309 powers back on and detects the discharged capacitor 313. In response, as shown in block 335, the detection module 309 updates a count of heat cycle events and saves the updated count to the data memory 311.

Figure 13:
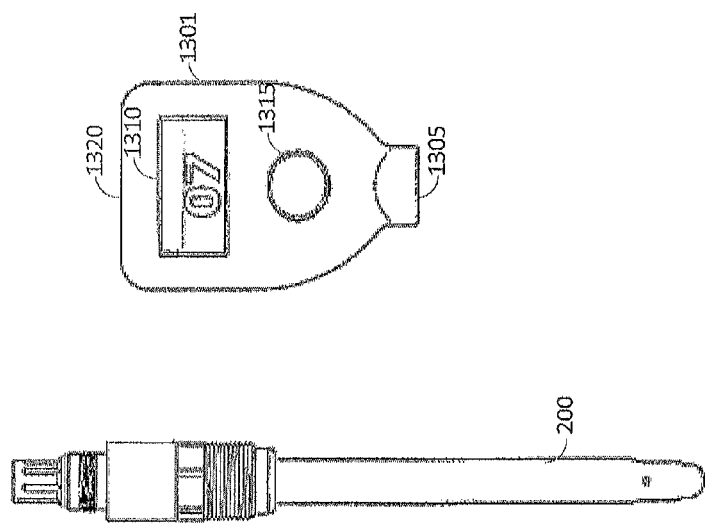
FIG. 13 depicts a diagram of an embodiment of a handheld device that may couple with a measurement device.

An additional embodiment of a measurement device is depicted schematically in FIG. 4A. As in the previous embodiment, the measurement device 400 includes a measurement probe 402 having a sensor 404 electrically coupled to a measurement interface 405 and a condition responsive element 406 electrically coupled to a heat cycle detection unit 408. In some embodiments, the condition responsive element 406 is located in the heat cycle detection unit 408, rather than the measurement probe 402. The heat cycle detection unit 408 includes a detection module 409, a data memory 411, and an interface 412. In the present embodiment, the detection module 409 is preferably a microprocessor programmed to control the heat cycle detection unit 408 and programmed to transform analog signals received from the condition responsive element 406 to digital signals. The interface 412 is preferably a wireless transmitter configured to output wireless signals, such as, for example, near-field communication, Bluetooth, Wi-Fi, or radiofrequency signals. The interface 412 of some embodiments includes multiple wireless transmitters capable of outputting multiple forms of wireless signals. In some embodiments, the wireless signals are received by, and displayed on, a handheld device having a display screen, as shown in FIG. 13 and described in more detail below. Additionally or alternatively, the interface 412 of some embodiments includes a data bus for wired digital outputs. In some embodiments, the interface 412 and interface 405 are the same interface.

In FIG. 4A, the capacitor 313 of FIG. 3A has been replaced with a battery 413. In other embodiments, the measurement device includes both a battery and a capacitor. In the depicted embodiment, the battery 413 is part of the heat cycle detection unit 408, disposed within a housing unit 414. In other embodiments, the battery 413 is electrically coupled to the detection module 409 but physically separable from the heat cycle detection unit 408. In some embodiments, the battery 413 is readily accessible to facilitate battery replacement. In some embodiments, the battery in FIG. 4A is a rechargeable battery. In other embodiments, a disposable battery is used. The battery 413 functions as a portable power source, thereby allowing at least some of the electronics within the measurement device 400 to remain powered when the device 400 is disconnected from an external power source. Consequently, the heat cycle detection unit 408 is configured to continue functioning when the measurement device 400 is placed within an autoclave chamber, or otherwise disconnected from an external power source, e.g. during a steam-in-place cycle. The embodiment of FIG. 4A additionally includes a power-gathering system 415. The power-gathering system 415 can include any portable element capable of converting energy from light into voltage or current, such as, for example, a photodiode or a photovoltaic cell. In the embodiment of FIG. 4A, a photodiode 415 is included to trickle charge the battery 413 to help maintain charge in the system.

FIG. 4B provides a flowchart depicting a method of counting exposures to sterilization or cleaning cycles performed by the detection module 409 of FIG. 4A. At block 440 the probe is disconnected from the external power supply and the internal battery continues to power the device. At block 441, the detection module 409, which is electrically coupled to the condition responsive element 406, receives a modified signal from the condition responsive element 406. In the embodiments of FIGS. 4A-4B, the condition responsive element 406 is an electrical resistive element, for example, a thermistor or RTD, which experiences significant changes in resistance with changing temperature. In other embodiments, the condition responsive element 406 is a pressure sensor, which generates a changed signal, for example, due to a change in resistance or inductance, as the internal probe pressure or surrounding pressure changes. The detection module 409 of various embodiments is configured to detect changes in the received signal. The detection module 409 is also programmed to determine, using known equations, when the changed signal indicates that a select threshold temperature or pressure has been reached.

In other embodiments (not shown), the condition responsive element is a condition responsive circuit that includes a thermal or pressure switch. In some such embodiments, when the temperature or pressure rises near or above a threshold level, the thermal switch or pressure switch changes state, causing the condition responsive circuit to open. The detection module (which receives power from a battery to which it is connected via an alternate circuit), detects the cessation of current in the condition responsive circuit. In other such embodiments, when the temperature or pressure rises near or above a threshold level, a thermal switch or pressure switch changes state, causing a condition responsive circuit to close. The detection module (which receives power from a battery to which it is connected via an alternate circuit), detects the flow of current in the condition responsive circuit. Through such mechanisms, the detection module, in effect, detects that the threshold temperature or pressure value has been reached.

As shown at block 442 and 443, when the detection module 409 detects that the threshold temperature or pressure has been reached, the count of heat cycle events is updated and saved in the data memory 411. In some embodiments, the detection module 409 increments a counter and stores the new count within the data memory 411. In other embodiments, the detection module 409 stores the date and, optionally, the time of heat cycle (e.g. autoclave) detection in the data memory 411.

To protect the circuitry from malfunctioning due to extreme temperatures and/or pressures, the detection module 409 then optionally powers down, as shown at block 444 (if the circuitry of the device can operate reliably and predictably under high temperature/pressure, the device need not power down). To better protect the circuitry, in some embodiments, a threshold temperature or pressure is selected that is lower than the ranges described above. For example, in biotechnology, measurement probes are often used to monitor processes occurring at a temperature range around 37 degrees Celsius, such as, for example, 35-40 degrees Celsius. In such industries, measurement devices may be selected having a threshold temperature of 60-70 degrees Celsius, for example. It will be appreciated by those having ordinary skill in the art that any threshold temperature or pressure may be selected for counting sterilization or cleaning cycles that is above the maximum temperature or pressure experienced by the measurement device during normal (non-sterilization or cleaning) operations.

Figure 5B:
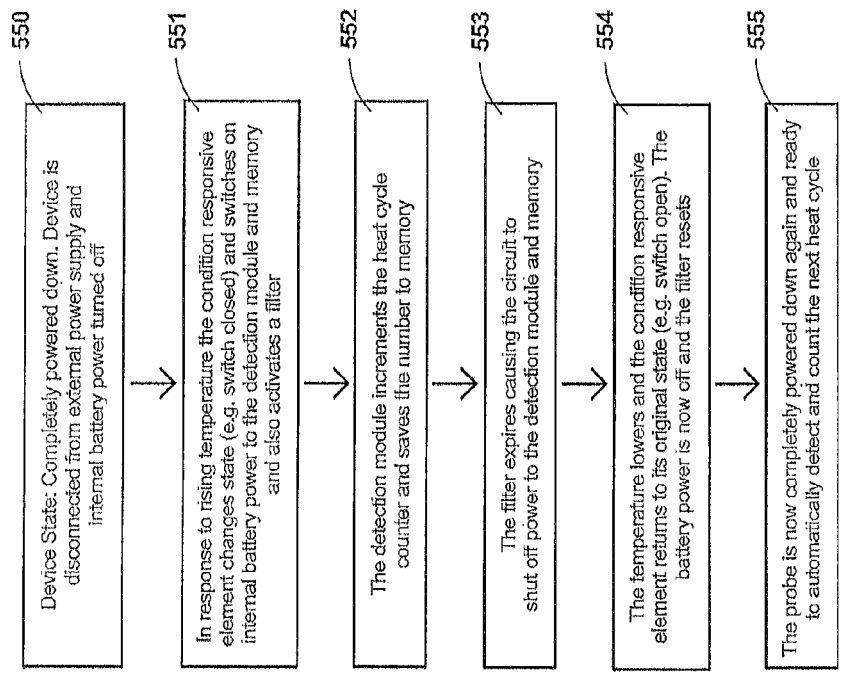
FIG. 5B is a flowchart illustrating one method of operations performed by the measurement device of FIG. 5A.
Figure 5A:
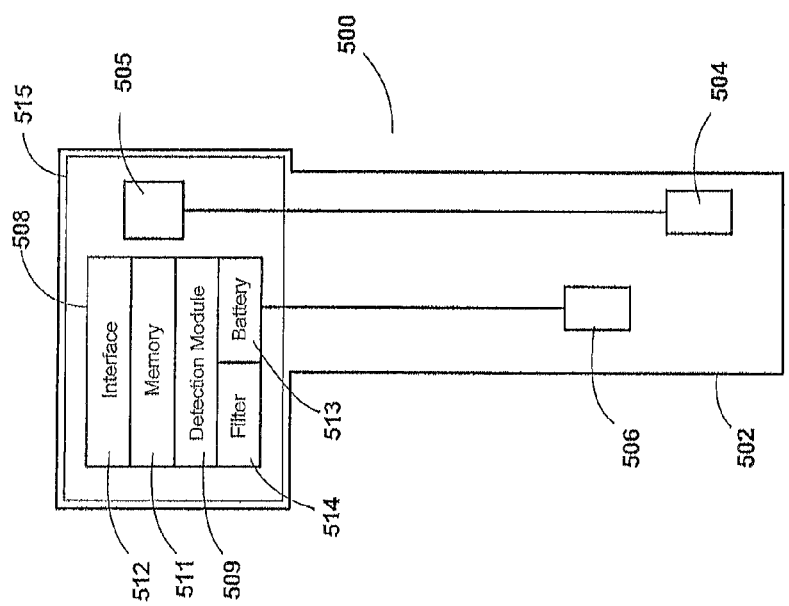
FIG. 5A depicts a block diagram of another embodiment of a measurement device.

An additional embodiment of a measurement device is depicted schematically in FIG. 5A. As in the previous embodiment 4A, the measurement device 500 includes a measurement probe 502 having a sensor 504 electrically coupled to a measurement interface 505 and a condition responsive element 506 electrically coupled to a heat cycle detection unit 508. In some embodiments, the condition responsive element 506 is located in the heat cycle detection unit 508, rather than the measurement probe 502. The heat cycle detection unit 508 includes a detection module 509, a data memory 511, and an interface 512. In the present embodiment, the detection module 509 is preferably a microprocessor programmed to control the heat cycle detection unit 508. The interface 512 is preferably a wireless transmitter configured to output wireless signals, such as, for example, near-field communication, Bluetooth, Wi-Fi, or radiofrequency signals. The interface 512 of some embodiments includes multiple wireless transmitters capable of outputting multiple forms of wireless signals. In some embodiments, the wireless signals are received by, and displayed on, a handheld device having a display screen (not shown in this figure, but shown in FIG. 13 and described in more detail below). Additionally or alternatively, the interface 512 of some embodiments includes a data bus for wired digital outputs. In some embodiments, the interface 512 and interface 505 are the same interface.

In FIG. 5A, the capacitor 313 of FIG. 3A may be replaced with a battery 513 and a signal filter element 514, such as a capacitor or similar charge storage element or a timer element. In the depicted embodiment, the battery 513 is part of the heat cycle detection unit 508, disposed within a housing unit 515. In other embodiments, the battery 513 is electrically coupled to the detection module 509 but physically separable from the heat cycle detection unit 508. In some embodiments, the battery in 513 is readily accessible to facilitate battery replacement. In some embodiments the battery in FIG. 5A is a rechargeable battery. In other embodiments, a disposable battery is used. The battery 513 functions as a portable power source, thereby allowing at least some of the electronics within the measurement device 500 to power up on its own when the device 500 is disconnected from an external power source. Consequently, the heat cycle detection unit 508 is configured to power on when the measurement device 500 is placed within an autoclave chamber (or otherwise disconnected from and external power source) and the condition responsive element 506 changes state when it exceeds its threshold limit.

FIG. 5B provides a flowchart depicting a method of counting exposures to sterilization or cleaning cycles performed by the detection module 509 of FIG. 5A. At block 550 the device has been disconnected from an external power source whereupon the device automatically powers down. At block 551, the condition responsive element 506, in this embodiment a thermal switch, changes state in response to the temperature rising above the threshold value. Another embodiment may replace the thermal switch with a pressure switch. This change in state closes (or alternatively opens, depending on the circuit architecture) the thermal switch which in turn supplies internal battery power 513 to the detection module 509 and the memory 511 and activates a signal filter, such as a timer 514, or charges a capacitor. Thus, the heat cycle detection module 508 may automatically power on. At block 552 the detection module 509 increments the heat cycle counter, and saves the new number in memory 511. In block 553, the timer expires or reaches a threshold time, or alternatively the capacitor completely charges, and this may cause power to be automatically shut off to the detection module and memory which in turn saves battery power and protects the microprocessor in 509 and other components of the detection unit 508 from operating in the excessive heat of an autoclave cycle. In block 554, the heat cycle event ends, the probe's temperature sinks back down past the threshold value of the thermal switch (or pressure switch) 506, the switch changes back to its original open state (or alternatively closed state, depending on the circuit architecture), the battery is disconnected from the circuit, and the timer resets, or the capacitor discharges. As a result of the automatic actions in block 554 the device is now in a state represented by block 555 where the device is now off, conserving the battery 513, and ready to automatically and autonomously power on again when the next heat cycle begins.

The signal filter 514 (e.g., a timer or capacitor element) serves the purpose of filtering signals from the condition responsive element 506, such that multiple changes in state of the condition responsive element during the period where the timer or capacitor element is activated, but time has not yet expired (or capacitor discharged) will not be counted as multiple heat cycles. For example, if the temperature or pressure fluctuates near the threshold of the condition responsive element, a the condition responsive element may change between states several times until the heat cycle event progresses past the threshold temperature or pressure sufficiently for the condition responsive element to remain in a changed state. By utilizing a timer or capacitor element, the device be ready to record a new heat cycle event only after the timer expires or reaches a threshold time (or the capacitor is discharged). Thus, the amount of time required to filter out these fluctuations will depend on the type of heat cycle and sensitivity of the condition responsive elements. One of skill in the art will be able to determine the required amount of time. It is contemplated that the amount of time will be from about 5 seconds to as much as 5 minutes, or 5 seconds to 2 minutes, or 30 seconds to 5 minutes. In some embodiments, the amount of time will be 0.1, 0.5, 1, 2, 3, 4, 5, 6, 7, 8, 9, 10, 15 minutes, or a range defined by any two of the preceding values. Filters other than the timer or capacitor element to filter the signal from the condition responsive element to avoid false heat cycle counts will be apparent to those of skill in the art.

Figures 6A, 6B:
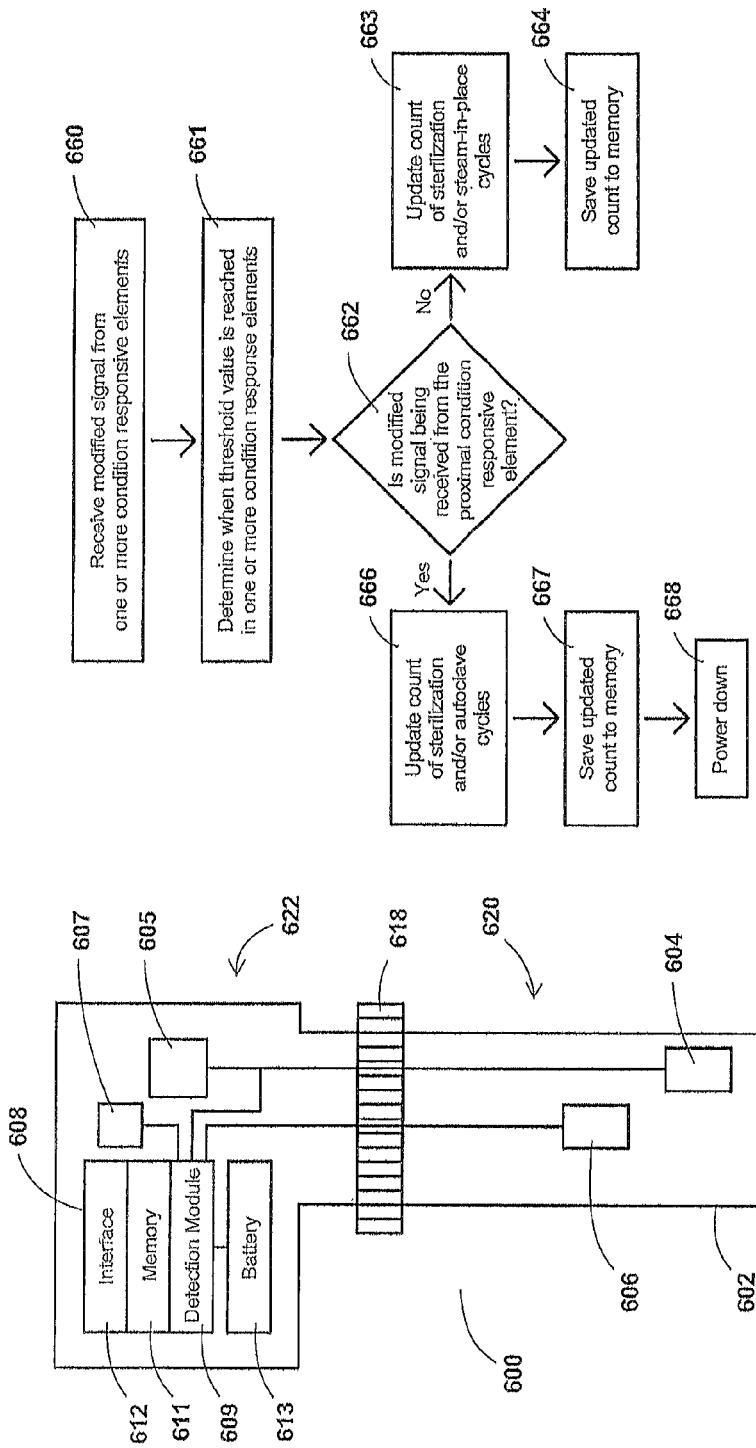
FIG. 6A depicts a block diagram of another embodiment of a measurement device.
FIG. 6B is a flowchart illustrating one method of operations performed by the measurement device of FIG. 6A.

FIG. 6A provides a schematic of another embodiment of a measurement device 600 having a battery 613 and a heat cycle detection unit 608. The heat cycle detection unit 608 includes a detection module 609, a data memory 611, and an interface 612. As in previous embodiments, the measurement device 600 also includes a measurement probe 602 with a sensor 604 electrically coupled to a measurement interface 605. In other embodiments, the sensor 604 is electrically coupled to the detection module 609. In such embodiments, the detection module 609 is configured to amplify the signal received from the sensor 604 and convert it to a digital output. The digital output can then be provided to an output device via the interface 612 in a similar manner as the sterilization or cleaning count data that is transmitted to an output device via the interface 612. In addition, in some embodiments a signal filter (e.g. capacitor or other charge storage unit, or timer) (not shown) is included and functions as described in FIG. 5.

The measurement device 600 of FIG. 6A also has a vessel coupling device 618, which is configured to secure the measurement device 600 to a perimeter wall or lid (i.e., the body) of a processing vessel. In various embodiments, the measurement device 600 is secured to the body of a processing vessel such that a distal portion 620 of the measurement device 600 is disposed within an interior cavity of the vessel and a proximal portion 622 of the measurement device 600 is positioned outside the vessel.

In some embodiments, the measurement device includes only one condition responsive element. In such embodiments, if the condition responsive element is a proximal condition responsive element, which is typically but not necessarily positioned on or within a proximal portion of the measurement device, it will not respond to temperature or pressure changes that occur within the processing vessel, if the proximal portion of the measuring device is sufficiently insulated from temperature and/or pressure of the distal portion of the measuring device. Consequently, if a steam-in-place cycle or clean-in-place cycle is run within the processing vessel, the proximal condition responsive element will not respond, and the sterilization or cleaning cycle will not be counted. In contrast, autoclaving requires placement of the entire measurement probe within an autoclave chamber. Consequently, a proximal condition responsive element will experience the elevated temperatures and pressures of an autoclave cycle. Thus, when only a proximal condition responsive element is used, the measurement device is tailored to count, specifically, autoclave cycles.

Conversely, if only one condition responsive element is present and it is a distal condition responsive element, typically but not necessarily located in the distal portion of the measurement device, the distal condition responsive device will be subjected to any elevated temperatures and pressures that occur within the processing vessel as well as elevated temperatures and pressures that occur while the measurement device is disposed within an autoclave chamber. In such embodiments, the measurement device is configured to detect and count multiple forms of sterilization or cleaning cycles, although it may not distinguish between the types of cycles detected. Each detected cycle is counted and stored in memory as a generic sterilization or cleaning cycle.

In some measurement device embodiments, such as the embodiment of FIG. 6A, the measurement device 600 includes both a distal condition responsive element 606, typically but not necessarily positioned on or within the distal portion 620 and a proximal condition responsive element 607, typically but not necessarily positioned on or within the proximal portion 622. Such embodiments may be configured to detect and count multiple forms of heat cycles and distinguish between the various forms. The detection of a response by the proximal condition responsive element 607 with or without a response by the distal condition responsive element 606 may indicate that an autoclave sterilization process is detected, and that detected cycle may be counted and stored in memory as an autoclave cycle. However, if the distal condition responsive element 606 responds but the proximal condition responsive element 607 does not respond, then the detected cycle is either a clean-in-place or a steam-in-place.

A method of detecting, distinguishing, and counting various forms of sterilization or cleaning is provided in the flowchart of FIG. 6B. As shown in block 660, the detection module 609 receives a modified signal from a condition responsive element 606 and/or 607 as the temperature or pressure rises. From the modifications in the signal, the detection module 609 determines when a threshold temperature or pressure has been reached, as shown in block 661. In block 662, the detection module 609 determines whether the modified signal is being received from the proximal condition responsive element 607. If it is, then the entire measurement device 600 is being subjected to an elevated temperature and/or pressure, and one can conclude that the measurement device 600 is in an autoclave chamber undergoing an autoclave cycle. In such cases, the detection module 609 is programmed to update a count of autoclave cycles (and/or a count of generic sterilization or cleaning cycles) as indicated in block 666, save the updated count in the data memory 611 as indicated in block 667, and optionally power down the detection module 609 to protect the electronics in the heat cycle detection unit 608 or save power, as indicated in block 668.

If the detection module 609 determines that the modified signal is not being received from the proximal condition responsive element 607, (and thus, is instead coming from only the distal condition responsive element 606), the detection module 609 is programmed to update a count of steam-in-place cycles (and/or a count of generic sterilization or cleaning cycles) as indicated in block 663, and save the updated count in the data memory 611 as indicated in block 664. The detection module 609 may optionally be programmed to power down in response to detecting the heat cycle, although such programming is not as important for steam-in-place cycles when the heat cycle detection unit electronics are located outside the processing vessel, although it may be desirable to power down to save battery power during the heat cycle process if the device is battery powered.

Figure 7B:
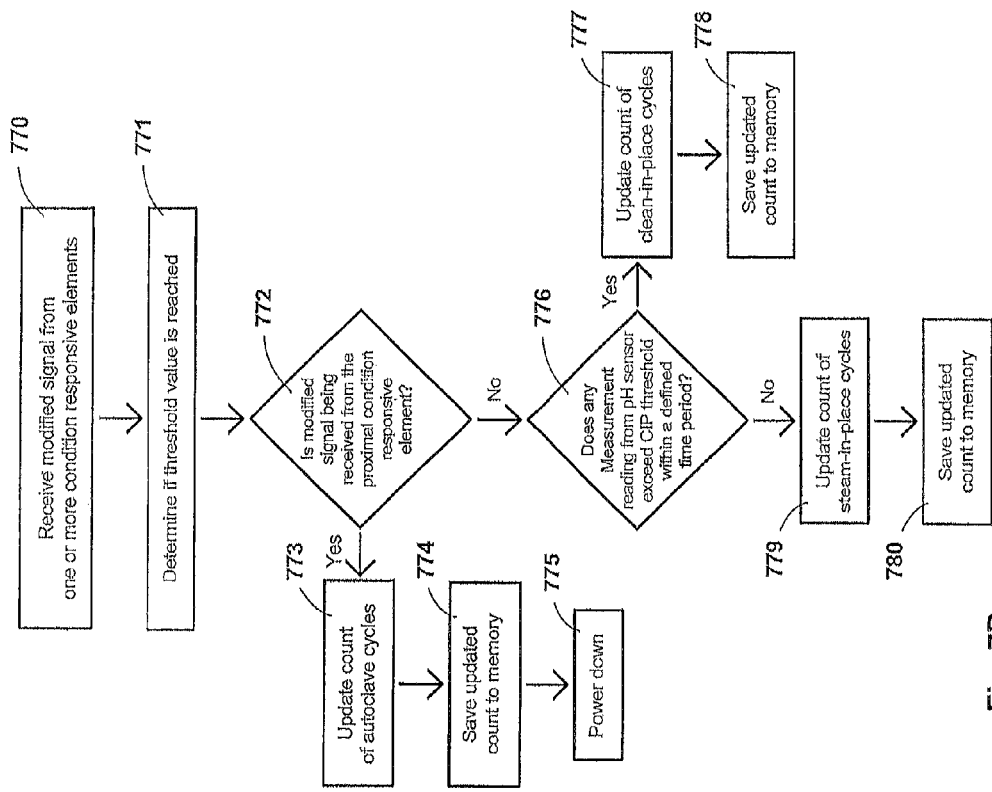
FIG. 7B is a flowchart illustrating one method of operations performed by the measurement device of FIG. 7A.
Figure 7A:
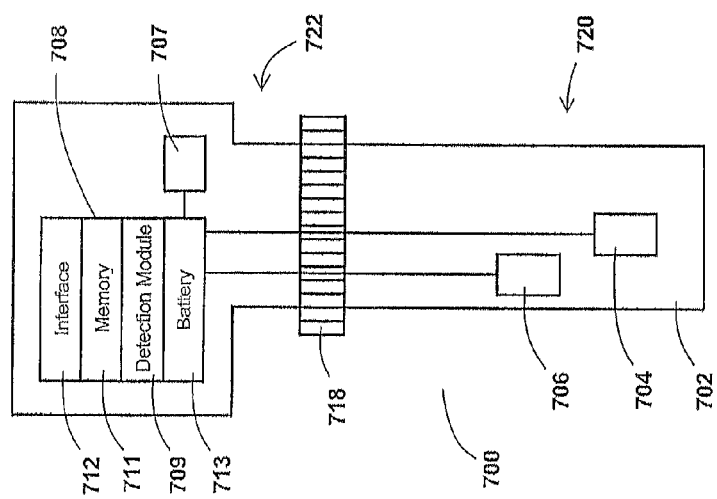
FIG. 7A depicts a block diagram of another embodiment of a measurement device.

FIG. 7A schematically depicts an embodiment of a measurement device 700 configured to detect clean-in-place cycles, along with, preferably, autoclave cycles. The provided measurement device 700 includes a heat cycle detection unit 708 having an interface 712, a data memory 711, a detection module 709, and a battery 713. The measurement device 700 also includes a measurement probe 702 having a pH sensor 704 disposed on or within the probe 702. The pH sensor 704 of the current embodiment is electrically coupled to the heat cycle detection unit 708. In some embodiments, the pH sensor 704 is provided to help detect clean-in-place cycles, and the measurement probe 702 includes one or more other sensors configured to sense a condition of the processing medium. In other embodiments, the pH sensor 704 serves as both the primary sensor of the measurement probe 702 and the sensor used during detection of clean-in-place cycles, and thus may be coupled to an interface (not shown) which is used during normal operation for monitoring pH levels.

In FIG. 7A, a vessel coupling device 718 is permanently or separably affixed to an outer portion of the measurement probe 702. A first distal temperature responsive element 706, is typically but not necessarily positioned on or within a distal portion 720 of the measurement device 700, and a proximal condition responsive element 707, is typically but not necessarily positioned on or within a proximal portion 722 of the measurement device 700.

FIG. 7B depicts one embodiment of a method performed by the measurement device of FIG. 7A when counting clean-in-place and other heat cycle events. The detection module 709 receives signals from one or more of the condition responsive elements 706 and 707, and the signals change as the temperature or pressure increases and/or crosses a threshold. As shown in blocks 770 and 771, detection module 709 receives a modified signal from at least one condition responsive unit, and from the signal, determines when a threshold value has been reached. The detection module 709 also performs the operation in block 772 to determine if the modified signal was received from the proximal condition responsive element 707. If it was, then the detection module 709 follows the autoclave detection protocol described previously. As shown in blocks 773-775, the detection module 709 updates a count of autoclave cycles, saves the updated count to the data memory 711, and optionally powers down (if the circuitry of the device can operate under high temperature/pressure, or conserving battery power is not desired/needed, the device need not power down). If the modified signal was not received from the proximal condition responsive element 707, (and thus, is instead coming from only the distal condition responsive element 706), the detection module 709 processes signal inputs from the pH sensor 704. In block 776, the device determines if any measurement reading from the pH sensor 704 exceeds a clean-in-place pH threshold within a defined time period, and if so, a clean-in-place detection protocol is performed (blocks 777-778). If no pH reading exceeds the clean-in-place threshold during the defined time period, the steam-in-place detection protocol is performed (block 779-780). The clean-in-place protocol, shown in blocks 777 and 778, involves updating a count of clean-in-place cycles and saving the updated count to the data memory 711. Similarly, the steam-in-place protocol, shown in blocks 779 and 780, includes updating a count of steam-in-place cycles and saving the updated count to the data memory 711. The detection module 709 can further be optionally programmed to shut down in response to detection of a steam-in-place cycle and/or a clean-in-place cycle, for example, to save battery power.

In some embodiments, the clean-in-place threshold is at least 60 degrees Celsius and less than 100 degrees Celsius. Typically, the clean-in-place threshold is between 65 and 90 degrees Celsius, and it can include any sub-range or individual value within that disclosed range, including 65, 70, 75, 80, 85 and 90 degrees Celsius. In some embodiments, the pH threshold is within the ranges of either 9 to 14 pH or 1 to 4 pH and may be any sub-range or individual value therebetween. For example, the clean-in-place pH threshold of some embodiments is 9, 10, 11, 12, 13, or 14. In some embodiments, the defined period of time is between about 30 seconds and about 5 minutes, and includes any sub-range or individual value therebetween, including 0.5-4, 0.5-3, 0.5-2, 1-5, 1-4, 1-3, 1-2, 2-5, 2-4, and 2-3 minutes. The defined period of time includes both the about 30 seconds to about 5 minutes preceding the temperature-threshold-reaching event and the about 30 seconds to about 5 minutes following the temperature-threshold-reaching event.

In some embodiments of a measurement device, the measurement device may comprise an autonomous smart monitoring system as described above. The measurement device may both automatically power on and automatically power itself off at certain points in a heat sterilization or cleaning, or autoclave cycle, without external control and power. This automatic power on and/or off feature may advantageously provide for more accurate counting of heat cycles as well as provide better power management of the battery and thus longer shelf life of the probe. For example, without an automatic power on feature in embodiments where cycle counts are only recorded after the device powers on, only one cycle will be counted if multiple successive heat cycles are performed on a measurement device without turning it on between cycles. In some embodiments, that cycle is counted during the cycle, just prior to the measurement device shutting down. In other embodiments, a cycle is counted when the measurement device powers back on, for example, by detecting a drained capacitor. By either method it is desirable to have the probe automatically power on whenever a heat cycle begins again. By automatically powering back on as a cycle starts, the measurement device of the current embodiment is ready to detect and count each new cycle that occurs. By use of a thermal switch as a condition responsive element the device can be configured to automatically power on each time there is a new heat cycle. Furthermore, since the device can automatically power on at the beginning of the heat cycle, there is no need to keep it on after the counter is incremented and the device can shut itself off for the remainder of the cycle to conserve the battery and protect the functionality of the microprocessor during excessive heat.

Figure 8:
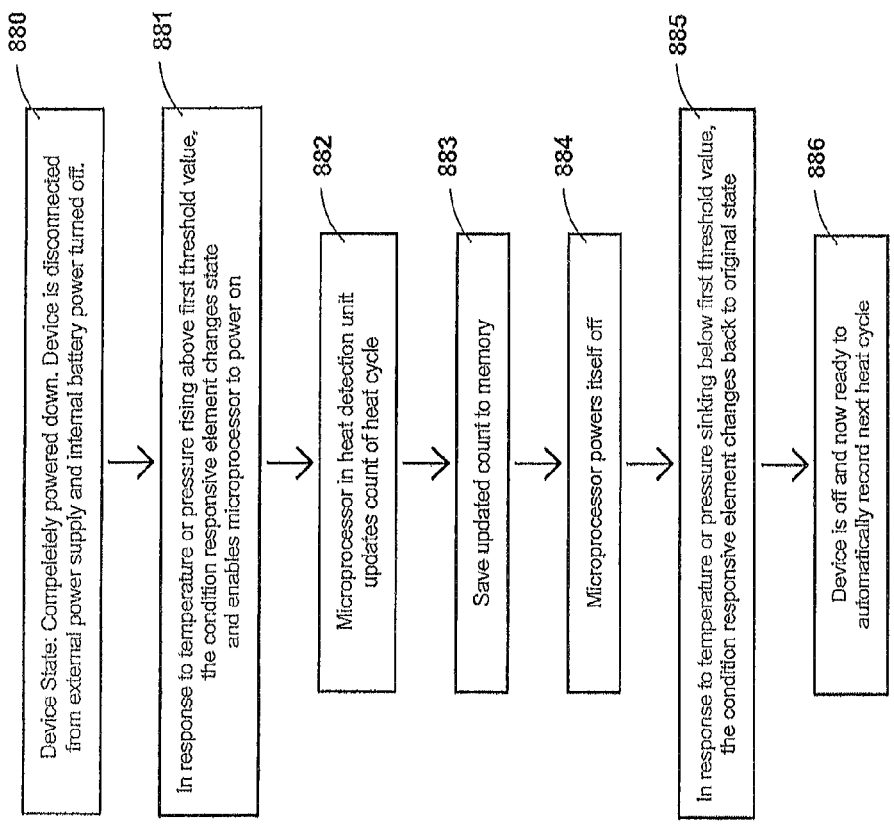
FIG. 8 depicts a block diagram of another embodiment of a measurement device.

Measurement device embodiments that perform the method of FIG. 8 include an integral power supply, such as a battery. In some embodiments, both a battery and a capacitor are included. In some embodiments the power supply is augmented by a portable power supply such as an attachable battery. In block 880 the device is in a state of complete power down. The device is disconnected from the external power supply and the internal battery power is turned off. In block 881 the condition responsive element changes state at a pre-determined temperature threshold (or pressure threshold), and switches power on to the device. In block 882 the detection module signals that a heat cycle has begun, for example by detecting that a capacitor has been discharged or charged in response to a change in state of the condition responsive element or by directly detecting the change of state of the condition responsive element itself. In block 883 the count is incremented by 1 in memory and saved. In block 884 the device powers off the microprocessor for it to better endure the extreme temperatures of an autoclave cycle and to conserve the internal battery. In block 885 the probe's temperature cools to below the temperature threshold (or pressure drops below the pressure threshold) of the condition responsive element, the element's state changes back to the original state. In block 886 the device is once again completely powered down and ready to automatically count the next heat cycle. Where a capacitor is present, it can be returned to its pre-cycle state, for example being recharged by the battery, and is thus ready for the next cycle.

Figure 9:
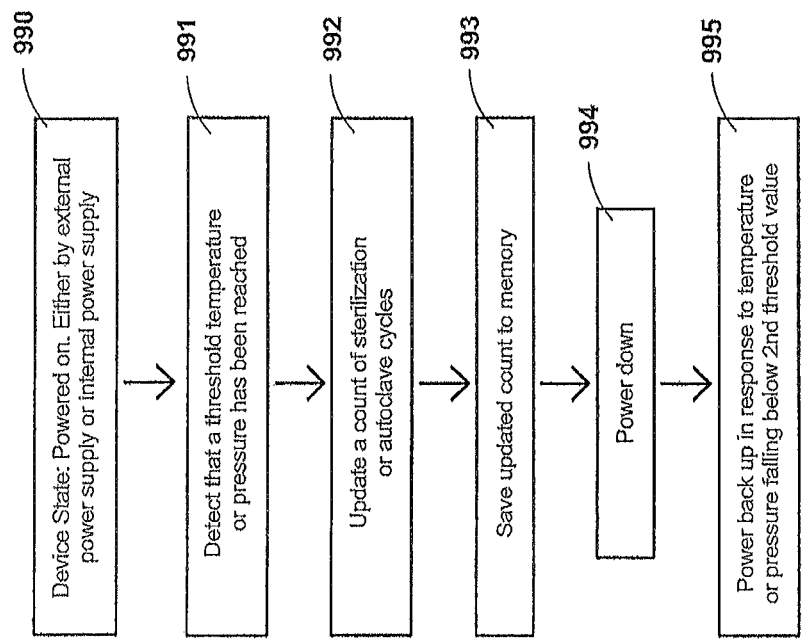
FIG. 9 depicts a block diagram of another embodiment of a measurement device.

Another method performed by some embodiments of a measurement device is provided in the flowchart of FIG. 9. In the depicted method, the measurement device can both automatically shut itself off and automatically turn itself back on at certain points in a heat sterilization or cleaning, e.g., autoclave cycle.

Measurement device embodiments that perform the method of FIG. 9 include a portable power supply, such as a battery. In some embodiments, both a battery and a capacitor are included. In block 990 at least the heat cycle detection portion of the device is powered on. As shown in blocks 991-994, the detection module of such measurement devices detects that a threshold temperature or pressure has been reached, updates a count of heat cycle event (e.g. autoclave), saves the updated count in the data memory, and optionally powers down (if the circuitry of the device can operate under high temperature/pressure, or battery power conservation is not desired, the device need not power down). In one embodiment, a thermal or pressure switch is used. When a threshold temperature or pressure is reached, the switch physically deforms and opens a circuit connecting the switch, capacitor, battery, and detection module. When this occurs, the battery no longer provides voltage and current to the detection module, and the capacitor or other charge storage unit begins to drain. The detection module receives current from the draining capacitor long enough to detect the opened switch and record the occurrence of a heat cycle event (sterilization or cleaning) in the data memory. The detection module powers down as the current wanes. As shown in block 995, when the temperature or pressure falls below a second threshold value (also referred to as a power-on temperature or pressure), the switch returns to its first, non-deformed position, which completes the circuit. Charge and voltage from the battery are again delivered to the detection module, and the detection module turns back on. In embodiments having one universal switch that functions to both power off and power on the detection module, the first threshold value and second threshold value are generally equal. Shape memory materials and bimetallic strips are generally configured to deform and reform to their original shapes at substantially similar or equal temperatures.

In an alternative embodiment, the detection module may perform blocks 991-994 in response to receiving a changing signal from an electrical condition responsive element. From the change in signal, the detection module is configured to calculate/detect that a first threshold value has been reached. In such an embodiment, a second condition responsive element in the form of a mechanical switch is included in a second circuit in the measurement device. The detection module is configured to automatically power up, as recited in block 995, when the mechanical switch changes state an electrical contact closed in the second circuit. This occurs when a second threshold value is reached. In such embodiments, the first threshold value may be the same or different than the second threshold value. In some embodiments, the counter increments after the heat cycle ends, rather than at the start of the heat cycle.

Figure 10:
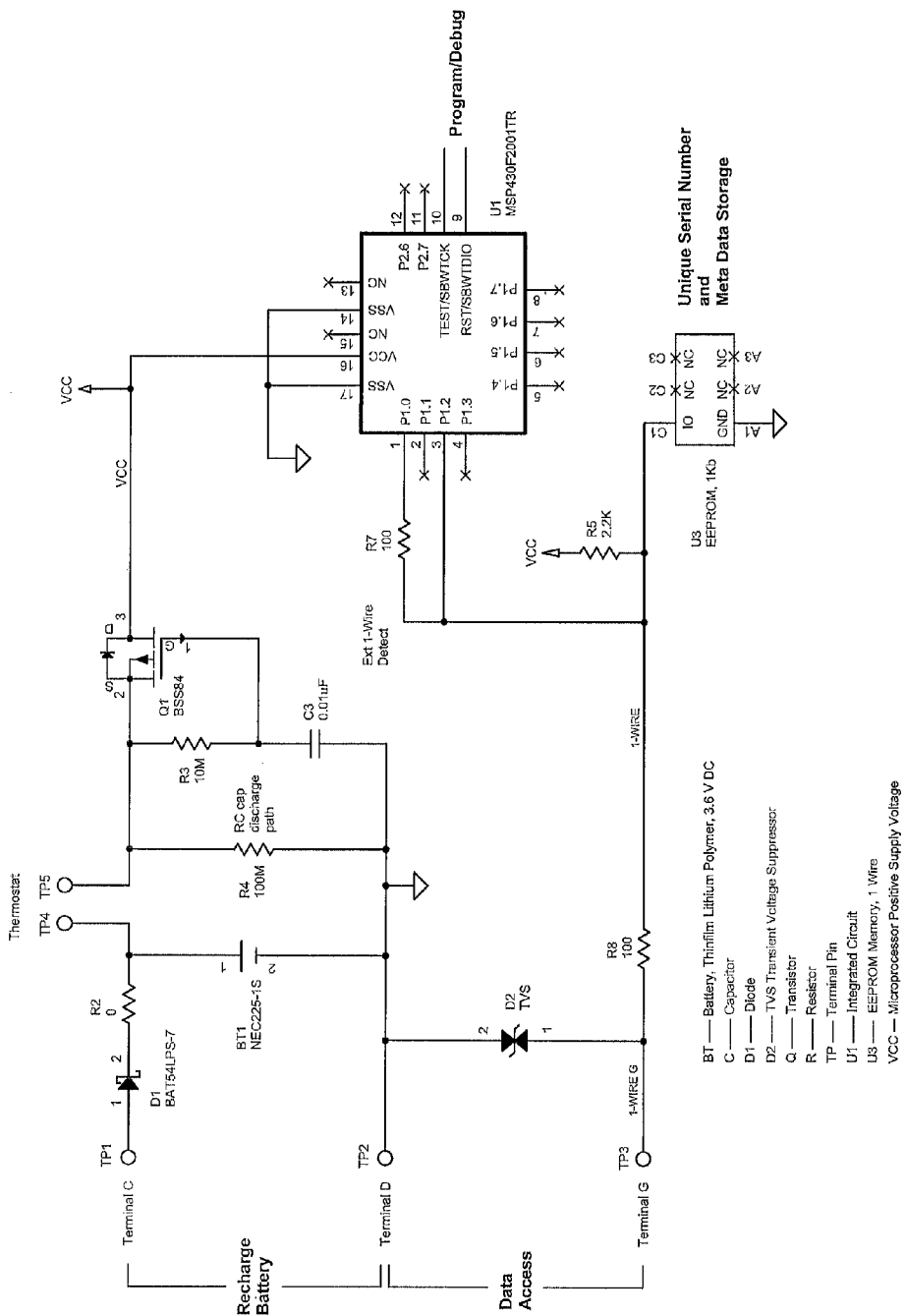
FIG. 10 depicts a circuit diagram for an embodiment of a heat cycle detection unit.

FIG. 10 depicts a circuit diagram of one embodiment of a heat cycle detection unit. This particular embodiment automatically detects and records heat cycles according to the embodiment described with reference to FIG. 5B. FIG. 11 is a schematic of a circuit diagram of one embodiment of a heat cycle detection unit.

Figure 12A:
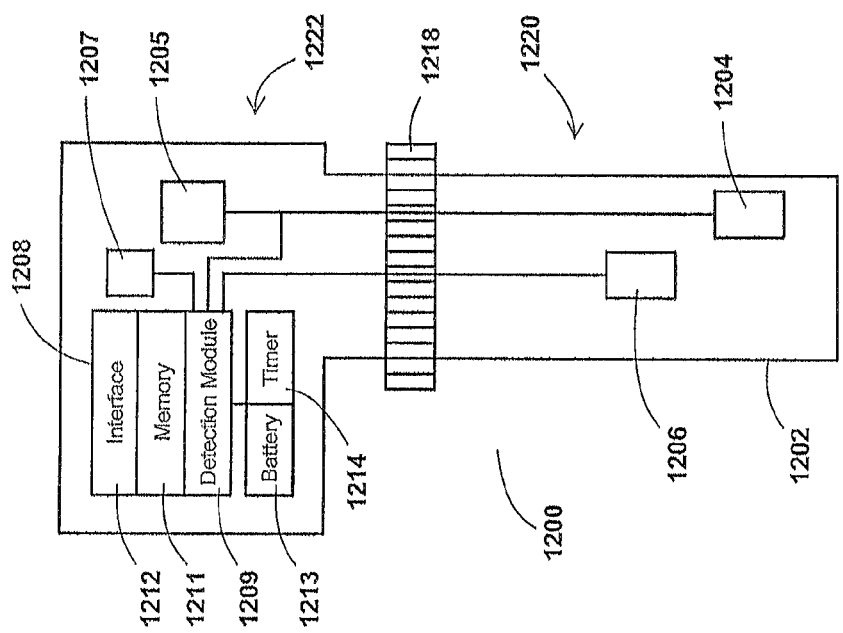
FIG. 12A depicts a block diagram of another embodiment of a measurement device.

FIG. 12A provides a schematic of another embodiment of a measurement device 1200 having a battery 1213 and a heat cycle detection unit 1208. The heat cycle detection unit 1208 includes a detection module 1209, a data memory 1211, and an interface 1212. As in previous embodiments, the measurement device 1200 also includes a measurement probe 1202 with a sensor 1204 electrically coupled to a measurement interface 1205. In other embodiments, the sensor 1204 is electrically coupled to the detection module 1209. In such embodiments, the detection module 1209 is configured to amplify the signal received from the sensor 1204 and convert it to a digital output. The digital, output can then be provided to an output device via the interface 1212 in a similar manner as the sterilization or cleaning count data that is transmitted to an output device via the interface 1212. In addition, in some embodiments a signal filter such as a timer 1214 is included and functions as described in FIGS. 5A and B.

The measurement device 1200 of FIG. 12A also has a vessel coupling device 1218, which is configured to secure the measurement device 1200 to a perimeter wall or lid (i.e., the body) of a processing vessel. In various embodiments, the measurement device 1200 is secured to the body of a processing vessel such that a distal portion 1220 of the measurement device 1200 is disposed within an interior cavity of the vessel and a proximal portion 1222 of the measurement device 1200 is positioned outside the vessel.

In some measurement device embodiments, such as the embodiment of FIG. 12A, the measurement device 1200 includes both a distal condition responsive element 1206, typically but not necessarily positioned on or within the distal portion 1220 and a proximal condition responsive element 1207, typically but not necessarily positioned on or within the proximal portion 1222. Such embodiments may be configured to detect and count multiple forms of heat cycles and distinguish between the various forms. In an embodiment, the condition responsive element 1207 may be an RTD. The detection of a response by the proximal condition responsive element 1207 with or without a response by the distal condition responsive element 1206 may indicate that an autoclave sterilization process is detected, and that detected cycle may be counted and stored in memory as an autoclave cycle. However, if the distal condition responsive element 1206 responds but the proximal condition responsive element 1207 does not respond, then the detected cycle is either a clean-in-place or a steam-in-place.

Figure 12B:
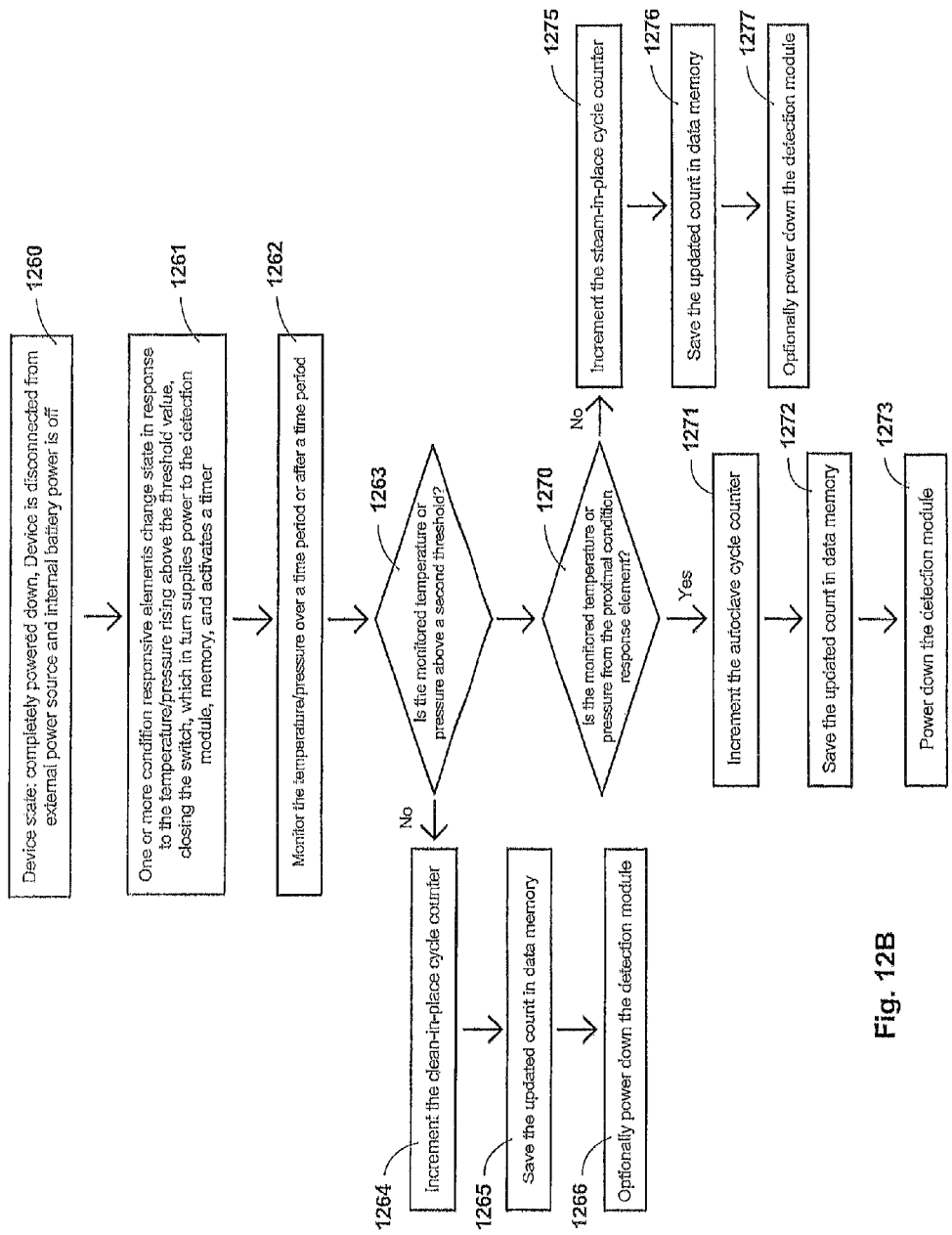
FIG. 12B is a flowchart illustrating one method of operations performed by the measurement device of FIG. 12A.

A method of detecting, distinguishing, and counting various forms of sterilization or cleaning is provided in the flowchart of FIG. 12B. At block 1260 the device has been disconnected from an external power source whereupon the device automatically powers down. At block 1261, one or more condition responsive elements 1206 and 1207, in this embodiment thermal switches, changes state in response to the temperature rising above the threshold value. This change in state closes the thermal switch which in turn supplies internal battery power 1213 to the detection module 1209 and the memory 1211 and activates a timer 1214. Thus, the heat cycle detection module 1208 may automatically power on. Another embodiment may replace the thermal switches with pressure switches.

The detection module 1209 monitors the temperature/pressure over a time period or after a time period, as shown in block 1262. The detection module 1209 determines whether a second threshold temperature or pressure which is higher than the first threshold has been reached by any of the condition responsive elements, as shown in block 1263. If the second threshold temperature or pressure has not been reached, then the detection module 1209 increments the clean-in-place cycle counter, as indicated in block 1264, saves the updated count in the data memory 1211 as indicated in block 1265, and optionally powers down the detection module 1209, as indicated in block 1266.

If the second threshold temperature or pressure has been reached, then the detection module 1209 must determine from which condition responsive element 1206 or 1207 the signal of the temperature or pressure exceeding the second threshold is being received, as indicated in block 1270. If the detection module 1209 determines that the temperature or pressure above the second threshold is being received from the proximal condition responsive element 1207, then the entire measurement device 1200 is being subjected to an elevated temperature and/or pressure, and one can conclude that the measurement device 1200 is in an autoclave chamber undergoing an autoclave cycle. In such cases, the detection module 1209 is programmed to update a count of autoclave cycles (and/or a count of generic sterilization or cleaning cycles) as indicated in block 1271, save the updated count in the data memory 1211 as indicated in block 1272, and power down the detection module 1209, as indicated in block 1273, although powering down is optionally not performed if protection of the device and/or power conservation is not an desired. If the detection module 1209 determines that the temperature or pressure above the second threshold is being received from the distal condition responsive element 1206 and not the proximal condition responsive element 1207, then only the distal portion of the measurement device 1200 is being subjected to an elevated temperature and/or pressure, and the measurement device 1200 is being subjected to a steam-in-place cycle. In such cases, the detection module 1209 is programmed to update a count of steam-in-place cycles (and/or a count of generic sterilization or cleaning cycles) as indicated in block 1275, save the updated count in the data memory 1211 as indicated in block 1276, and optionally power down the detection module 1209, as indicated in block 1277.

In an alternate embodiment, the condition responsive element may be used in conjunction with a heat detection unit RTD responsive to temperature changes in and/or around the distal portion of the measurement device (a "distal RTD"). The distal RTD may operate, after powering up due to a condition responsive element changing state in response to the temperature/pressure rising above a threshold value, to determine if the heat cycle event is a clean-in-place cycle or a higher temperature cycle, such as a steam-in-place or autoclave cycle. The distal RTD used to analyze the heat cycle event may be independent from any RTD used by the measurement device. In an alternate embodiment, the distal RTD used by the heat cycle detection unit is also used by the measurement device.

In another embodiment, a distal condition responsive element may be installed along with a heat detection unit RTD responsive to temperature changes in and/or around the distal portion of the measurement device (a "distal RTD"), with an additional heat detection unit RTD responsive to temperature changes in and/or around the proximal portion of the measurement device (a "proximal RTD"). Thus, the distal RTD, preferably located in the distal portion of the measurement device, may function as a distal condition response element, while the proximal RTD, preferably located in the proximal portion of the measurement device, may function as a proximal condition response element. In this embodiment, the two RTDs may be evaluated together to determine the type of heat cycle event. The two RTDs may function similarly to the discussion above regarding proximal and distally condition response elements and detection of clean-in-place, steam-in-place, and autoclave cycles. Thus, when the proximal RTD temperature is above a threshold temperature and the distal RTD is either above or below the threshold temperature, the heat cycle counter will increment the autoclave cycle count. If the distal RTD registers above a threshold but the proximal RTD is below a threshold, then the heat cycle counter will increment either a clean-in-place or a steam-in-place, dependent upon the distal RTD temperature reading. As discussed above, the distal RTD used to analyze the heat cycle event may be independent from any RTD used by the measurement device. In an alternate embodiment, the distal RTD used by the heat cycle detection unit is also used by the measurement device.

FIG. 13 depicts a diagram of an embodiment of a handheld device that may couple with a measurement device. In some embodiments, the handheld device 1300 described above may be configured to physically couple to any of the measurement devices disclosed herein, including devices 100, 200, 300, 400, 500, 600, or 700, and electrically couple to the respective interfaces (for example, interface 212, 312, 412, 512, 612, or 712, respectively). For simplicity, measurement device 200 and interface 212 will be used to describe the functionality of the handheld device 1300. However, any discussion related to the handheld device 1300 and the measurement device 200 and interface 212 will be understood to apply to any other of the measurement devices disclosed herein, e.g., measurement devices 100, 200, 300, 400, 500, 600, or 700 and their respective interfaces.

The handheld device 1300 comprises a circuit board enclosed within a housing 1301. The housing 1301 may comprise cutouts for a connector 1305, a screen 1310, and one or more buttons 1315. In some embodiments, the housing 1301 may further comprise a cutout for a connector (or cable) 1320 and/or one or more additional connectors 1305. The housing 1301 may be formed of a material that isolates and insulates the enclosed circuit board from external forces and events. In embodiments having connectors 1305, the housing 1301 may comprise removable caps or covers configured to provide a sealed enclosure when the caps or covers are affixed over or within the connectors 1305. The circuit board enclosed within the housing 1301 may comprise an energy source (for example a battery), energy source connector, or energy storage device configured to provide power to the handheld device 1300 and any connected measurement device 200. The circuit board may also comprise all the circuits and components necessary to perform the functions of the handheld device 1300 described herein. In some embodiments, the handheld device 1300 may not comprise any connectors 1305 and may instead communicate with other devices (for example, the measurement device 200 or an external computing device via any wireless communication method). In some embodiments, the handheld device 1300 may be capable of both wireless communication and communication via connectors 1305. In some embodiments, the handheld device 1300 may comprise a communication circuit. The communication circuit may comprise one or more components that enable the handheld device 1300 to communicate with one or more measurement devices 200 or external computing devices. The communication circuit may enable the handheld device 1300 to communicate via any connected, wired, or wireless methods (for example via copper contacts, via a network cable, or via wireless communications).

In some embodiments, the housing 1301 may be generally rectangular with contours and beveled edges leading to the connector 1305, which may be located at a bottom surface of the housing 1301. The screen 1310 may be rectangular and situated on a front surface of the housing 1301. The screen 1310 may be located closer to a top surface of the housing 1301 and may be framed by the housing 1301. The button 1315 may be circular and may be situated below the screen 1310 and above the bottom surface.

In some embodiments, the handheld device 1300 may comprise the connector 1305 configured to create physical and electrical connections with the measurement device 200, for example via a VarioPin connector and/or VarioPin cables. In some embodiments, the connector 1305 may be integrated with a cable (not shown in this figure) connected to the handheld device 1300. In other embodiments, the connector 1305 is instead a protruding connector (not shown in this figure) that may couple with a connector on the measurement device 200 with which the handheld device 1300 is being coupled. Other physical connectors known in the art may be used, e.g., as shown in FIG. 13, the connector may comprise a receptacle configured to receive a connector from a cable or a sensor. In other embodiments, the handheld device 1300 may comprise a wireless communication means (not shown in this figure, for example, as Bluetooth communication device, an infrared communication device, a radio frequency communication device, or a wireless communication device) configured to allow for wireless communication with the interface 212 (or interface 412, wherein the interface 212 is configured to participate in wireless communications. In some embodiments, the handheld device 1300 may comprise both the connector 1305 and one or more wireless communication means.

In some embodiments, the handheld device 1300 may further comprise the screen 1310, wherein the screen 1310 may be configured to display information received by the handheld device 1300 from the measurement device 200. For example, the screen 1310 may display information regarding the number of heat cycle counts detected by the measurement device 200 or may display identifying information regarding the connected measurement device 200, for example a serial number of the measurement device 200 or a user established identifier, for example, a part number or a device name in the user's control system. In some embodiments, the handheld device 1300 may be configured to automatically extract or read information from the connected measurement device 200 and display that information on the screen 1310. For example, when the measurement device 200 is connected to the handheld device 1300, the screen 1310 may automatically display the measurement device 200 identifying information (for example, the serial number or user device name, as described above) or the total sterilization cycles count (for example, including one or more of an autoclave cycle count, a steam-in-place cycle count, a clean-in-place cycle count, etc.).

In some embodiments, while the one or more cycle counts are displayed on the screen 1310 of the handheld device 1300, the button 1315 (or other input means, for example a switch, a touch sensor, a light sensor) may be actuated to clear or reset a selected cycle count field. In some embodiments, the handheld device 1300 may be configured to display a different field associated with information from the measurement device 200 when the button 1315 is actuated. For example, the screen 1310 may display autoclave cycle counts when the measurement device 200 is initially connected to the handheld device 1300. In some embodiments, the single button 1315 may be replaced with multi-directional single button that may be configured to allow multiple actuations from a single physical button 1315 (for example, a single button 1315 with directional arrows for use in navigating through menus, etc.).

Actuation of the button 1315 may cause the screen 1310 to display the identifying information for the measurement device 200 or calibration parameters of the measurement device 200 (for example, the slope, offset, or % efficiency). In some embodiments, the button 1315 may be actuated to display on the screen 1310 manufacturing data of the connected measurement device 200 or the handheld device 1300 itself. For example, the screen 1310 may be used to display manufacturing data including the serial number of the measurement device 200, a manufacturer's part number of the measurement device 200, performance data of the measurement device 200, or date of calibration or other tests performed on the measurement device 200. Similar information may be displayed on the screen 1310 regarding the handheld device 1300 (for example, serial number, part number, manufacturing date, etc.). In some embodiments, the screen 1310 may be configured to display user data fields stored in either the measurement device 200 or the handheld device 1300. These user data fields may comprise a measurement device name or tag, an experiment name, an operator name, a lot number, or a free form field that may be used for storage of any information desired by the user.

In some embodiments, the handheld device 1300 may be unable to receive and display measurement data from the measurement device 200. In such embodiments, the handheld device 1300 may be configured to receive and display only sterilization cycle counts of the measurement device 200, calibration parameters of the measurement device 200, manufacturing data of the measurement device 200, and customer customizable data fields of the measurement device 200.

In some embodiments, the connector 1320 may comprise a connector that allows the handheld device 1300 to be physically connected to a computer or some other external computing device (for example, a smartphone, a laptop computer, or a third party configuration device). For example, the connector 1320 may comprise an USB port, a Firewire port, or any other unidirectional or bidirectional physical communication interface. In some embodiments, the wireless communication means described above as allowing wireless communications with the interface 212 (or, for example, interface 412 and/or interface 512, described above as being capable of wireless communication) of the measurement device 200 may also be used to allow wireless communication with the external computing device instead of or in addition to using the connector 1320. Connecting the handheld device 1300 to the external computing device via the connector 1320 or wirelessly may allow the user to write data to the user data fields of the measurement device 200 or review information stored in the measurement device 200 or the handheld device 1300. In some embodiments, connecting the handheld device 1300 to the external computing device may allow the user to calibrate the measurement device 200 using any known calibration technique (for example, two point calibration) via the handheld device 1300. In some embodiments, the handheld device 1300 may be configured to allow calibration of the measurement device 200 without being connected to the external computing device (for example, allow the user to calibrate the measurement device 200 using only the handheld device 1300).

The handheld device 1300 may slip onto the connector of the measurement device 200 and may instantly read data stored in the measurement device 200. In some embodiments, the handheld device 1300 may default to first displaying the sterilization cycle count for the connected measurement device 200. In some embodiments, the handheld device 1300 may default to displaying a menu of available options or fields for viewing related to the measurement device 200. In some embodiments, the data read by the handheld device 1300 (when physically connected or when wirelessly connected) may comprise non-measurement data from the measurement device 200, for example, heat sterilization cycle counts or calibration information. In some embodiments, the handheld device 1300 may be further configured to read measurement data from the measurement device 200, for example, the measured pH from a pH measurement device 200.

In some embodiments, the handheld device 1300 may be configured to allow copying of information from a first measurement device 200 to a second measurement device 200. In some embodiments, the first measurement device 200 and the second measurement device may both be connected to the handheld device 1300 at the same time. In some embodiments, the first and second measurement devices 200 may be connected one after the other, wherein the handheld device 1300 may be configured to store data from the first measurement device 200 to be sent to the second measurement device 200 at a later time. Such capabilities of the handheld device 1300 may allow the user to replace the first measurement device 200 with the second measurement device 200 and copy all parameters from the first measurement device 200 to the second measurement device 200 to simplify the replacement process. For example, the customer data fields or any parameter fields may all be copied. In some embodiments, the calibration parameters may be copied via the process described above. In some embodiments, the current number of cycle counts may be copied via the process described above.

In some embodiments, one or both of the handheld device 1300 and/or the measurement device 200 may be configured to power on automatically when the handheld device 1300 is connected to the measurement device 200. When the handheld device 1300 is powered on when either connected to the measurement device 200 or disconnected from the measurement device 200, it may be configured to automatically power off after a predetermined amount of time if no button 1315 is actuated and no measurement device 200 is connected or disconnected from the connector 1305. In some embodiments, the handheld device 1300 may be configured to automatically power off when the measurement device 200 is disconnected from the connector 1305. In some embodiments, the predetermined amount of time before the automatic power off or power on may be user adjustable. For example, the predetermined amount of time may be set to five minutes before the user adjusts it to a larger or smaller amount of time. In some embodiments, the handheld device 1300 may be configured to automatically power on when the button 1315 is actuated even when no measurement device 200 is connected to the handheld device 1300. In such an instance, the handheld device 1300 may be configured to display information associated with the most recently connected measurement device 200. In some embodiments, once automatically powered on, the user may be able to cycle through the various fields and parameters of the handheld device 1300 by actuating the button 1315.

In some embodiments, the handheld device 1300 may comprise a memory that may be configured to store or save information read from one or more previously connected measurement devices 200. In some embodiments, when a new measurement device 200 is connected to the handheld device 1300, the information read from the new measurement device 200 may automatically replace the stored information in the memory. When the handheld device 1300 is powered on when no measurement device 200 is connected, the screen 1310 and the button 1315 may be used by the user to browse information for any measurement device 200 stored in the memory of the handheld device 1300. In some embodiments, the memory of the handheld device 1300 may be used to store information entered by the user in relation to the measurement device 200, for example the name of the measurement device 200 or the location or point of installation of the measurement device 200.

In some embodiments, the handheld device 1300 may be designed to provide a user with a device providing the ability to individually monitor a plurality of measurement devices 200 at the point of installation of the measurement devices 200. The portable nature of the handheld device 1300 may prevent damage of the measurement device 200 that may be caused by uninstalling or installing the measurement device 200 at its point of use. Additionally, the handheld device 1300 may minimize errors that may be inherent in collecting a plurality of measurement devices 200 from multiple points of installation and monitoring them at a centralized location, for example, reinstalling the measurement devices at wrong points of use, mixing up the measurement devices while monitoring information from them, etc. For example, the handheld device 1300 may receive and display information comprising identification information of the measurement device 200. Alternatively, or additionally, the handheld device 1300 may receive and display the sterilization cycle count of the measurement device or the location of installation of the measurement device 200. The handheld device 1300 may receive and display one or more calibration parameters of the measurement device 200, one or more manufacturing data of the measurement device 200, and/or customer specific information of the measurement device.

The handheld device 1300 may provide instant, pushbutton access to internal memory of measurement devices 200 to allow for quick inspection by the user of the measurement device 200's sterilization cycle count, calibration status, battery life, and usage information. The handheld device 1300 may allow the user to access all information useful in synchronizing the measurement device to an external and autonomous system or integrating advanced or new measurement devices with existing control systems without needing to upgrade or replace existing control system equipment. For example, a large biopharmaceutical company may have an existing array of bioreactor control systems and equipment, for example, having 100 pH meters, all of the control systems and equipment being in good working order. The control systems and equipment may represent a large investment. However, one or more of the bioreactor control systems or other equipment may not be fully compatible with the measurement devices 200 that store digital information in internal memory and, thus, may be unable to make use of the additional functionality of the measurement devices 200. Accordingly, specialized equipment or proprietary software may be required by the bioreactor control systems or other equipment to communicate with and fully integrate and make use of the measurement devices 200 in the existing bioreactor control systems and equipment. Thus, accessing information from the measurement device 200 and controlling the measurement device 200 using the existing control systems and equipment may be inefficient and troublesome. Additionally, updating the control systems and equipment may be unrealistic and a wasted cost.

Instead of updating the control systems and equipment, the handheld device 1300 may be used to integrate the measurement device 200 with use with existing control system and equipment. The handheld device 1300 may allow users with an existing infrastructure to take advantage of additional functionalities of the measurement devices 200 (for example, having memory for storage of digital, operational information) without having to invest substantial amounts in new control systems or equipment. The handheld device 1300 may provide an inexpensive and self-sufficient device that does not require any separate computing device, software, or application to communicate with and read information from the measurement devices 200. The handheld device 1300 may be designed to interface directly with the measurement device 200 and display the stored information in an intuitive and convenient manner. Thus, the handheld device 1300 may allow the user to utilize the additional functionalities of the measurement device 200 while the existing control system and equipment may interface with and utilize the measurement data and other previously existing functionalities of the measurement device 200. Additionally, another example of a benefit of the handheld device 1300 may include the ability to determine a misplaced measurement device 200 where its history or use is unknown. An additional example of a benefit may be the ability read or write information to the measurement device 200 without removing the measurement device 200 from its position of use in the autonomous system.

The handheld device 1300 and the measurement device 200 may form a system configured to provide the user with the heat sterilization cycle count of the measurement device 200. In some embodiments, the user may connect a computing device to the handheld device 1300 and calibrate the measurement device 200 connected to the handheld device 1300, view and edit information stored in the measurement device 200, and view and edit information stored in the handheld device 1300.

The various operations and methods described above may be performed by any suitable means capable of performing the operations, such as various hardware and/or software component(s), circuits, and/or module(s). Generally, any operations illustrated in the Figures may be performed by corresponding functional means capable of performing the operations.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this invention has been described in connection with what is are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Thus, while the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A system, comprising:
    a measurement device adapted to withstand and automatically count a heat sterilization or cleaning cycle, comprising:
        a measurement probe comprising a sensor configured to detect a characteristic of a medium and generate a measurement signal;
        a condition responsive element comprising either a temperature responsive element or a pressure responsive element; and
        a heat cycle detection unit comprising a detection module, a data interface, and a data memory; wherein the detection module is configured to:
            detect a heat cycle event using the condition responsive element, and
            record detection of the heat cycle event in the data memory,
        wherein the measurement device is configured to automatically power off the heat cycle detection unit after detection of the heat cycle; and
    a handheld device connected to the measurement device, the handheld device comprising:
        a screen;
        a button;
        a communication circuit configured to communicate with the measurement device and a computing device; and
        a processing system configured to receive non-measurement information from the measurement device, display the received information on the screen, and cycle the received information displayed on the screen based on an actuation of the button,
    wherein the handheld device is used to display a heat cycle event count of the measurement device.

2. The system of claim 1, wherein the handheld device may communicate with the computing device and be configured to perform at least one of calibrating the measurement device via the computing device, viewing information stored in the measurement device via the computing device, editing information stored in the measurement device via the computing device, viewing information stored in the handheld device via the computing device, and editing information stored in the handheld device via the computing device.

3. The system of claim 1, wherein the handheld device is further used to display one or more of calibration parameters of the measurement device, manufacturing data of the measurement device, and customer custom fields of the measurement device.

4. The system of claim 1, wherein the handheld device further comprises a battery or an external power source, wherein the battery or external power source is configured to provide electrical power to the screen, the processing system, and the measurement device.

5. The system of claim 4, wherein the external power source comprises an inductive or other wireless power source configured to wirelessly transfer power to at least one of the handheld device and the measurement device.

6. The system of claim 1, wherein the handheld device further comprises a memory configured to store the information received from the measurement device and information entered by a user via the button or the computing device.

7. The system of claim 1, wherein the information received by the handheld device from the measurement device comprises one or more of an identification information of the measurement device, a heat cycle event count of the measurement device, a location of installation of the measurement device, one or more calibration parameters of the measurement device, one or more manufacturing data of the measurement device, and customer specific information of the measurement device.

8. The system of claim 7, wherein the one or more manufacturing data comprises a serial number, a manufacturer part number, performance data, and a date of calibration and performance tests.

9. The system of claim 7, wherein the customer specific information comprises an experiment name with which the measurement device is associated, an operator's name with which the measurement device is associated, a lot number with which the measurement device is associated, and one or more customer defined fields.

10. The system of claim 1, wherein the handheld device is further configured to receive data measured by the measurement device.

11. The system of claim 1, wherein the handheld device further comprises one or more connectors via which communications with one or more of the measurement device and the computing device are enabled, wherein the one or more connectors allow for physical and electrical connections between the handheld device and the one or more of the measurement device and the computing device.

12. The system of claim 1, wherein the measurement device is configured to automatically power on the heat cycle detection unit at the beginning of the heat cycle in response to a change of state of the condition responsive element.

13. The system of claim 1, wherein the measurement device further comprises a physical, optical, inductive, and/or wireless coupling connector, and wherein said physical, optical, inductive, and/or wireless coupling connector is configured to permit transfer of at least one of energy, power, and data via physical, optical, inductive and/or wireless coupling between the measurement device and at least one of an external power supply or transmitter.

14. The system of claim 1, wherein the handheld device is reversibly connected to the measurement device.

15. The system of claim 14, wherein the reversible connection is a physical, optical, inductive, and/or wireless connection.

16. A method of automatically counting and displaying a heat cycle experienced by a measurement device, comprising:
   detecting a heat cycle event experienced by the measurement device using a condition responsive element, the measurement device comprising:
      a measurement probe having a sensor configured to detect a characteristic of a medium and generate a measurement signal,
      a heat cycle detection unit having a detection module, a data interface, and a data memory, and
      the condition responsive element;
   recording detection of the heat cycle event in the data memory;
   communicating information to a handheld device via a reversible physical, optical, inductive, and/or wireless connection between the measurement device and the handheld device; and
   displaying the information from the measurement device on a screen of the handheld device,
   wherein the information displayed comprises at least one of a heat cycle event count of the measurement device and one or more identifying information or calibration parameters of the measurement device.

17. The method of claim 16, wherein the measurement device is configured to automatically power on the heat cycle detection unit at the beginning of the heat cycle in response to a change of state of the condition responsive element or automatically power off the heat cycle detection unit at the beginning of the heat cycle after detection of the heat cycle event.

18. The method of claim 16, wherein the measurement device comprises a battery and a capacitor, the method further comprising charging the capacitor from the battery when the measurement device automatically powers on, automatically powering off the heat cycle detection unit when the capacitor is charged, and discharging the capacitor when the condition responsive element indicates the heat cycle event is substantially complete.

19. The method of claim 16, wherein the condition responsive element is a first switch that transitions from a first state to a second state when the first switch exceeds a first temperature or a first pressure, and the detection module records detection of a heat cycle event in the data memory in response to the first switch transitioning from the first state to the second state.

20. The method of claim 16, wherein the measurement device further comprises a second condition responsive element, wherein said second condition responsive element is a second switch configured to transition from a power-on state to a power-off state when the second switch reaches a power-off temperature or pressure, and wherein the heat cycle detection unit automatically power offs when the second switch transitions from the power-on state to the power-off state.

21. The method of claim 16, wherein the detection module detects a heat cycle event and records detection of the heat cycle event in the data memory in response to either a proximal condition responsive element exceeding a first temperature or first pressure or a distal condition responsive element exceeding a vessel sterilization temperature or pressure.

22. The method of claim 16, wherein detecting a heat cycle event and recording detection of the heat cycle event in the data memory comprises:
   detecting an autoclave cycle and recording detection of the autoclave cycle in the data memory in response to a proximal condition responsive element exceeding a first temperature or a first pressure, and
   detecting a steam-in-place cycle and recording detection of the steam-in-place cycle in the data memory in response to a distal condition responsive element exceeding a vessel sterilization temperature or pressure and the proximal condition responsive element not exceeding the first temperature or the first pressure.

* * * * *